US011944522B2

(12) United States Patent
Greening, II et al.

(10) Patent No.: US 11,944,522 B2
(45) Date of Patent: Apr. 2, 2024

(54) ABSORBENT ARTICLE WITH EAR PORTION

(71) Applicant: The Procter & Gamble Company, Cincinnati, OH (US)

(72) Inventors: Nelson Edward Greening, II, Cincinnati, OH (US); Erica Lynne Locke, Cincinnati, OH (US); Urmish Popatlal Dalal, Milford, OH (US); Marcus Schönbeck, Versmold (DE); Maria Oude-Lansink, Gronau (DE); Jan Michael Trinkaus, Euskirchen (DE); Marius Janas, Oberhausen (DE); Marcel Grossmann, Essen (DE)

(73) Assignee: The Procter & Gamble Company, Cincinnati, OH (US)

( * ) Notice: Subject to any disclaimer, the term of this patent is extended or adjusted under 35 U.S.C. 154(b) by 947 days.

(21) Appl. No.: 16/916,655

(22) Filed: Jun. 30, 2020

(65) Prior Publication Data

US 2021/0000656 A1    Jan. 7, 2021

Related U.S. Application Data

(60) Provisional application No. 62/869,063, filed on Jul. 1, 2019.

(51) Int. Cl.
*A61F 13/47*    (2006.01)
*A61F 13/15*    (2006.01)
(Continued)

(52) U.S. Cl.
CPC .. *A61F 13/15203* (2013.01); *A61F 13/15699* (2013.01); *A61F 13/49011* (2013.01);
(Continued)

(58) Field of Classification Search
CPC .... A61F 13/47; A61F 13/62; A61F 13/15203; A61F 13/15699; A61F 13/49011;
(Continued)

(56) References Cited

U.S. PATENT DOCUMENTS 3,113,225 A    12/1963    Claus
3,338,992 A    8/1967    Allison
(Continued)

FOREIGN PATENT DOCUMENTS

CN    103209828 A    7/2013
CN    104582945 A    4/2015
(Continued)

OTHER PUBLICATIONS

All Office Actions; U.S. Appl. No. 17/195,677, filed Mar. 9, 2021.
(Continued)

*Primary Examiner* — Catharine L Anderson
*Assistant Examiner* — Ilya Y Treyger
(74) *Attorney, Agent, or Firm* — Daniel S. Albrecht; Wednesday G. Shipp

(57) ABSTRACT

An absorbent article includes a first waist region, a second waist region and a crotch region disposed between the first and second waist regions. The absorbent article further includes a topsheet, a backsheet, an absorbent core disposed between the topsheet and the backsheet, and a laminate. The laminate has an elasticized region. The laminate includes a first nonwoven, a second nonwoven and an elastomeric material sandwiched between said first and second nonwovens in the elasticized region. The laminate includes a bonding region with a bond density of at least 4% and at least partially overlapping the elastomeric material. The laminate exhibits an Unload Force at 50% of at least 0.90 N.

20 Claims, 13 Drawing Sheets

(51) Int. Cl.
  *A61F 13/49* (2006.01)
  *A61F 13/511* (2006.01)
  *A61F 13/514* (2006.01)
  *A61F 13/53* (2006.01)
  *A61F 13/51* (2006.01)
  *A61F 13/62* (2006.01)

(52) U.S. Cl.
  CPC .......... *A61F 13/511* (2013.01); *A61F 13/514* (2013.01); *A61F 13/53* (2013.01); *A61F 2013/15422* (2013.01); *A61F 2013/15869* (2013.01); *A61F 2013/49098* (2013.01); *A61F 2013/5108* (2013.01)

(58) Field of Classification Search
  CPC ...... A61F 13/511; A61F 13/514; A61F 13/53; A61F 2013/15422; A61F 2013/15869; A61F 2013/49098; A61F 2013/5108; A61F 13/4902; A61F 13/49014
  See application file for complete search history.

(56) References Cited

U.S. PATENT DOCUMENTS

| | | |
|---|---|---|
| 3,562,041 A | 2/1971 | Robertson |
| 3,566,726 A | 3/1971 | Politis |
| 3,692,613 A | 9/1972 | Pederson |
| 3,733,238 A | 5/1973 | Long |
| 3,802,817 A | 4/1974 | Matsuki |
| 3,848,594 A | 11/1974 | Buell |
| 3,849,241 A | 11/1974 | Butin |
| 3,860,003 A | 1/1975 | Buell |
| 3,911,173 A | 10/1975 | Sprague, Jr. |
| 3,929,135 A | 12/1975 | Thompson |
| 4,116,892 A | 9/1978 | Schwarz |
| 4,324,314 A | 4/1982 | Beach et al. |
| 4,405,297 A | 9/1983 | Appel |
| 4,463,045 A | 7/1984 | Ahr et al. |
| 4,515,595 A | 5/1985 | Kievit |
| 4,573,986 A | 3/1986 | Minetola et al. |
| 4,610,678 A | 9/1986 | Weisman |
| 4,629,643 A | 12/1986 | Curro |
| 4,634,440 A | 1/1987 | Widlund |
| 4,662,875 A | 5/1987 | Hirotsu |
| 4,673,402 A | 6/1987 | Weisman |
| 4,699,622 A | 10/1987 | Toussant |
| 4,710,189 A | 12/1987 | Lash |
| 4,780,352 A | 10/1988 | Palumbo |
| 4,785,996 A | 11/1988 | Ziecker et al. |
| 4,834,735 A | 5/1989 | Alemany |
| 4,834,741 A | 5/1989 | Sabee |
| 4,842,666 A | 6/1989 | Werenicz |
| 4,846,815 A | 7/1989 | Scripps |
| 4,854,984 A | 8/1989 | Ball |
| 4,888,231 A | 12/1989 | Angstadt |
| 4,892,536 A | 1/1990 | DesMarais et al. |
| 4,894,060 A | 1/1990 | Nestegard |
| 4,919,738 A | 4/1990 | Ball et al. |
| 4,940,464 A | 7/1990 | Van Gompel et al. |
| 4,946,527 A | 8/1990 | Battrell |
| 4,990,147 A | 2/1991 | Freeland |
| 5,006,394 A | 4/1991 | Baird |
| 5,037,416 A | 8/1991 | Allen |
| 5,092,861 A | 3/1992 | Nomura |
| 5,137,537 A | 8/1992 | Herron |
| 5,143,679 A | 9/1992 | Weber |
| 5,147,345 A | 9/1992 | Lavon |
| 5,149,720 A | 9/1992 | Desmarais |
| 5,151,092 A | 9/1992 | Buell |
| 5,156,793 A | 10/1992 | Buell et al. |
| 5,167,897 A | 12/1992 | Weber et al. |
| 5,221,274 A | 6/1993 | Buell |
| 5,242,436 A | 9/1993 | Weil |
| 5,246,433 A | 9/1993 | Hasse |
| 5,260,345 A | 11/1993 | Desmarais |
| 5,266,392 A | 11/1993 | Land et al. |
| 5,269,775 A | 12/1993 | Freeland |
| 5,340,648 A | 8/1994 | Rollins et al. |
| 5,342,338 A | 8/1994 | Roe |
| 5,344,691 A | 9/1994 | Hanschen |
| 5,360,420 A | 11/1994 | Cook et al. |
| 5,376,430 A | 12/1994 | Swenson et al. |
| 5,382,400 A | 1/1995 | Pike |
| 5,387,207 A | 2/1995 | Dyer |
| 5,397,316 A | 3/1995 | Young |
| 5,418,045 A | 5/1995 | Pike |
| 5,422,172 A | 6/1995 | Wu |
| 5,433,715 A | 7/1995 | Tanzer et al. |
| 5,501,756 A | 3/1996 | Rollins et al. |
| 5,507,909 A | 4/1996 | Rollins et al. |
| 5,518,801 A | 5/1996 | Chappell et al. |
| 5,554,145 A | 9/1996 | Roe |
| 5,569,234 A | 10/1996 | Buell |
| 5,571,096 A | 11/1996 | Dobrin |
| 5,580,411 A | 12/1996 | Nease |
| 5,591,155 A | 1/1997 | Nishikawa |
| 5,599,335 A | 2/1997 | Goldman et al. |
| 5,607,414 A | 3/1997 | Richards et al. |
| 5,607,760 A | 3/1997 | Roe |
| 5,609,587 A | 3/1997 | Roe |
| 5,622,772 A | 4/1997 | Stokes |
| 5,628,097 A | 5/1997 | Benson et al. |
| 5,635,191 A | 6/1997 | Roe |
| 5,643,588 A | 7/1997 | Roe |
| 5,658,639 A | 8/1997 | Curro et al. |
| 5,665,300 A | 9/1997 | Brignola |
| 5,674,216 A | 10/1997 | Buell et al. |
| 5,691,034 A | 11/1997 | Krueger |
| 5,700,254 A | 12/1997 | McDowall et al. |
| 5,702,551 A | 12/1997 | Huber et al. |
| 5,707,468 A | 1/1998 | Arnold |
| 5,804,021 A | 9/1998 | Abuto et al. |
| 5,817,199 A | 10/1998 | Brennecke et al. |
| 5,827,909 A | 10/1998 | Desmarais |
| 5,865,823 A | 2/1999 | Curro |
| 5,897,545 A | 4/1999 | Kline |
| 5,916,661 A | 6/1999 | Benson et al. |
| 5,957,908 A | 9/1999 | Kline |
| 5,968,025 A | 10/1999 | Roe |
| 5,968,888 A | 10/1999 | Blandiaux |
| 5,972,806 A | 10/1999 | Weinberger |
| 5,993,432 A | 11/1999 | Lodge et al. |
| 6,004,306 A | 12/1999 | Robles |
| 6,030,373 A | 2/2000 | Vangompel |
| 6,036,796 A | 3/2000 | Halbert |
| 6,077,375 A | 6/2000 | Kwok |
| 6,096,668 A | 8/2000 | Abuto |
| 6,107,537 A | 8/2000 | Elder |
| 6,118,041 A | 9/2000 | Roe et al. |
| 6,120,487 A | 9/2000 | Ashton |
| 6,120,489 A | 9/2000 | Johnson |
| 6,123,792 A | 9/2000 | Samida |
| 6,140,551 A | 10/2000 | Niemeyer |
| 6,153,209 A | 11/2000 | Vega et al. |
| 6,169,151 B1 | 1/2001 | Waymouth et al. |
| 6,200,635 B1 | 3/2001 | Kwok |
| 6,235,137 B1 | 5/2001 | Van Eperen et al. |
| 6,255,236 B1 | 7/2001 | Cree |
| 6,310,154 B1 | 10/2001 | Babcock |
| 6,361,634 B1 | 3/2002 | White et al. |
| 6,369,121 B1 | 4/2002 | Catalfamo |
| 6,410,129 B2 | 6/2002 | Zhang |
| 6,426,444 B2 | 7/2002 | Roe et al. |
| 6,428,526 B1 | 8/2002 | Heindel |
| 6,432,098 B1 | 8/2002 | Kline et al. |
| 6,454,989 B1 | 9/2002 | Neely |
| 6,458,447 B1 | 10/2002 | Cabell |
| 6,465,073 B1 | 10/2002 | Morman |
| 6,472,045 B1 | 10/2002 | Morman |
| 6,472,084 B1 | 10/2002 | Middlesworth |
| 6,475,600 B1 | 11/2002 | Morman |
| 6,498,284 B1 | 12/2002 | Roe |
| 6,508,641 B1 | 1/2003 | Kubik |
| 6,513,221 B2 | 2/2003 | Vogt |

(56) References Cited

U.S. PATENT DOCUMENTS

| | | |
|---|---|---|
| 6,518,378 B2 | 2/2003 | Waymouth et al. |
| 6,520,237 B1 | 2/2003 | Bolyard, Jr. et al. |
| 6,534,149 B1 | 3/2003 | Daley et al. |
| 6,540,854 B2 | 4/2003 | Couillard |
| 6,551,294 B1 | 4/2003 | Elsberg et al. |
| 6,555,643 B1 | 4/2003 | Rieger |
| 6,559,262 B1 | 5/2003 | Waymouth et al. |
| 6,561,430 B2 | 5/2003 | Ou |
| 6,572,595 B1 | 6/2003 | Klemp |
| 6,572,598 B1 | 6/2003 | Ashton |
| 6,582,518 B2 | 6/2003 | Riney |
| 6,586,652 B1 | 7/2003 | Roe et al. |
| 6,610,161 B2 | 8/2003 | Erdman |
| 6,610,390 B1 | 8/2003 | Kauschke |
| 6,613,146 B2 | 9/2003 | Bolyard, Jr. |
| 6,617,016 B2 | 9/2003 | Zhang et al. |
| 6,627,564 B1 | 9/2003 | Morman |
| 6,627,787 B1 | 9/2003 | Roe et al. |
| 6,632,386 B2 | 10/2003 | Shelley |
| 6,645,330 B2 | 11/2003 | Pargass |
| 6,645,569 B2 | 11/2003 | Cramer et al. |
| 6,649,001 B2 | 11/2003 | Heden |
| 6,652,693 B2 | 11/2003 | Burriss et al. |
| 6,677,258 B2 | 1/2004 | Carroll |
| 6,692,477 B2 | 2/2004 | Gibbs |
| 6,713,159 B1 | 3/2004 | Blenke et al. |
| 6,719,846 B2 | 4/2004 | Nakamura et al. |
| 6,737,102 B1 | 5/2004 | Saidman et al. |
| 6,758,925 B1 | 7/2004 | Stegelmann |
| 6,767,420 B2 | 7/2004 | Stegelmann |
| 6,818,083 B2 | 11/2004 | Mcamish et al. |
| 6,825,393 B2 | 11/2004 | Roe et al. |
| 6,830,800 B2 | 12/2004 | Curro |
| 6,843,134 B2 | 1/2005 | Anderson et al. |
| 6,849,142 B1 | 2/2005 | Goulait |
| 6,861,571 B1 | 3/2005 | Roe et al. |
| 6,863,933 B2 | 3/2005 | Cramer et al. |
| 6,878,433 B2 | 4/2005 | Curro |
| 6,905,488 B2 | 6/2005 | Olson |
| 6,974,514 B2 | 12/2005 | Hamulski |
| 7,056,404 B2 | 6/2006 | McFall et al. |
| 7,062,983 B2 | 6/2006 | Anderson et al. |
| 7,108,759 B2 | 9/2006 | You |
| 7,112,621 B2 | 9/2006 | Rohrbaugh et al. |
| 7,270,861 B2 | 9/2007 | Broering |
| 7,291,239 B2 | 11/2007 | Polanco |
| 7,435,243 B2 | 10/2008 | Miyamoto |
| 7,531,233 B2 | 5/2009 | Kling |
| 7,569,039 B2 | 8/2009 | Matsuda |
| 7,572,249 B2 | 8/2009 | Betts |
| 7,582,075 B2 | 9/2009 | Betts |
| 7,625,363 B2 | 12/2009 | Yoshimasa |
| 7,741,235 B2 | 6/2010 | Hashimoto |
| 7,803,244 B2 | 9/2010 | Siqueira |
| 7,806,883 B2 | 10/2010 | Fossum |
| 7,819,853 B2 | 10/2010 | Desai |
| 7,824,594 B2 | 11/2010 | Qureshi |
| 7,870,651 B2 | 1/2011 | Middlesworth |
| 7,896,641 B2 | 3/2011 | Qureshi |
| 7,917,985 B2 | 4/2011 | Dorsey |
| 7,931,632 B2 | 4/2011 | Betts |
| 7,954,213 B2 | 6/2011 | Mizutani |
| 7,998,127 B2 | 8/2011 | Betts |
| 8,062,279 B2 | 11/2011 | Miyamoto |
| 8,062,572 B2 | 11/2011 | Qureshi |
| 8,092,438 B2 | 1/2012 | Betts |
| 8,118,801 B2 | 2/2012 | Macura |
| 8,158,043 B2 | 4/2012 | Gibson |
| 8,172,971 B2 | 5/2012 | Yamamoto |
| 8,186,296 B2 | 5/2012 | Brown et al. |
| 8,361,913 B2 | 1/2013 | Siqueira |
| 8,450,557 B2 | 5/2013 | Nishitani |
| 8,454,571 B2 | 6/2013 | Rezai |
| 8,480,642 B2 | 7/2013 | Betts |
| 8,491,557 B2 | 7/2013 | Kline |
| 8,491,742 B2 | 7/2013 | Waas |
| 8,496,775 B2 | 7/2013 | Deng |
| 8,502,013 B2 | 8/2013 | Zhao |
| 8,518,004 B2 | 8/2013 | Betts |
| 8,585,666 B2 | 11/2013 | Weisman et al. |
| 8,618,350 B2 | 12/2013 | Mansfield |
| 8,679,391 B2 | 3/2014 | Odonnell |
| 8,690,852 B2 | 4/2014 | Macura |
| 8,697,938 B2 | 4/2014 | Roe |
| 8,709,579 B2 | 4/2014 | Hoenigmann |
| 8,728,051 B2 | 5/2014 | Lu et al. |
| 8,741,083 B2 | 6/2014 | Wennerback |
| 8,776,856 B2 | 7/2014 | Yamamoto |
| 8,795,809 B2 | 8/2014 | Mansfield |
| 8,858,523 B2 | 10/2014 | Sauer |
| 8,939,957 B2 | 1/2015 | Raycheck et al. |
| 8,940,116 B2 | 1/2015 | Gilgenbach |
| 9,102,132 B2 | 8/2015 | Wennerbck |
| 9,169,384 B2 | 10/2015 | Autran |
| 9,211,221 B2 | 12/2015 | Macura |
| 9,301,889 B2 | 4/2016 | Miyamoto |
| 9,333,125 B2 | 5/2016 | Kline et al. |
| 9,358,161 B2 | 6/2016 | Lawson et al. |
| 9,434,143 B2 | 9/2016 | Sablone |
| 9,498,941 B2 | 11/2016 | Sablone |
| 9,533,067 B2 | 1/2017 | Schonbeck |
| 9,687,580 B2 | 6/2017 | Schonbeck |
| 9,724,248 B2 | 8/2017 | Hughes |
| 9,821,542 B2 | 11/2017 | Bruce |
| 10,485,713 B2 | 11/2019 | Schonbeck |
| 10,524,964 B2 | 1/2020 | Sauer |
| 10,561,537 B2 | 2/2020 | Lenser et al. |
| 10,568,775 B2 | 2/2020 | Lenser |
| 10,568,776 B2 | 2/2020 | Lenser |
| 10,575,993 B2 | 3/2020 | Lenser |
| 10,588,789 B2 | 3/2020 | Surushe |
| 10,617,573 B2 | 4/2020 | Koshijima |
| 10,799,396 B2 | 10/2020 | Takeuchi |
| 10,959,887 B2 | 3/2021 | Lenser et al. |
| 10,966,876 B2 | 4/2021 | Lenser et al. |
| 11,071,654 B2 | 7/2021 | Lenser et al. |
| 11,083,633 B2 | 8/2021 | Lenser et al. |
| 11,135,100 B2 | 10/2021 | Schönbeck et al. |
| 11,179,278 B2 | 11/2021 | Schönbeck et al. |
| 11,266,543 B2 | 3/2022 | Lenser et al. |
| 11,331,223 B2 | 5/2022 | Lenser et al. |
| 11,382,798 B2 | 7/2022 | Lenser et al. |
| 11,642,250 B2 | 5/2023 | Lenser et al. |
| 2001/0018579 A1 | 8/2001 | Klemp |
| 2001/0024940 A1 | 9/2001 | Cook et al. |
| 2002/0095129 A1 | 7/2002 | Friderich |
| 2002/0187696 A1* | 12/2002 | Veiga ............... B32B 27/04 442/76 |
| 2002/0188268 A1 | 12/2002 | Kline |
| 2003/0021951 A1 | 1/2003 | Desai |
| 2003/0105446 A1 | 6/2003 | Hutson |
| 2003/0109843 A1 | 6/2003 | Gibbs |
| 2003/0109844 A1 | 6/2003 | Gibbs |
| 2003/0120240 A1 | 6/2003 | Buell |
| 2003/0124310 A1 | 7/2003 | Ellis |
| 2003/0148684 A1 | 8/2003 | Cramer et al. |
| 2003/0181120 A1 | 9/2003 | Wu |
| 2003/0233082 A1 | 12/2003 | Kline |
| 2004/0087235 A1 | 5/2004 | Morman |
| 2004/0091693 A1 | 5/2004 | Thomas |
| 2004/0102125 A1 | 5/2004 | Morman |
| 2004/0112509 A1 | 6/2004 | Morman |
| 2004/0121690 A1 | 6/2004 | Mleziva |
| 2004/0182499 A1 | 9/2004 | Collier |
| 2004/0209042 A1 | 10/2004 | Peacock |
| 2004/0224132 A1 | 11/2004 | Roe |
| 2005/0008839 A1 | 1/2005 | Cramer et al. |
| 2005/0065487 A1 | 3/2005 | Graef et al. |
| 2005/0107764 A1 | 5/2005 | Matsuda et al. |
| 2005/0154362 A1 | 7/2005 | Warren et al. |
| 2005/0222546 A1 | 10/2005 | Vargo |
| 2005/0245162 A1 | 11/2005 | Mccormack |
| 2005/0287892 A1 | 12/2005 | Fouse |
| 2006/0062963 A1 | 3/2006 | Middlesworth |

(56) References Cited

U.S. PATENT DOCUMENTS

| | | |
|---|---|---|
| 2006/0089616 A1 | 4/2006 | Belau et al. |
| 2006/0135024 A1 | 6/2006 | Thomas |
| 2006/0148361 A1 | 7/2006 | Mccormack |
| 2006/0149209 A1 | 7/2006 | Malchow |
| 2006/0271003 A1 | 11/2006 | Loescher |
| 2006/0287637 A1 | 12/2006 | Lam |
| 2007/0048497 A1 | 3/2007 | Zhou et al. |
| 2007/0105472 A1 | 5/2007 | Marche |
| 2007/0123124 A1 | 5/2007 | Middlesworth |
| 2007/0141311 A1 | 6/2007 | Mleziva |
| 2007/0142798 A1 | 6/2007 | Goodlander |
| 2007/0142806 A1 | 6/2007 | Roe |
| 2007/0142825 A1 | 6/2007 | Prisco |
| 2007/0143972 A1 | 6/2007 | Kline |
| 2007/0202767 A1 | 8/2007 | Anderson |
| 2007/0219521 A1 | 9/2007 | Hird et al. |
| 2007/0234529 A1 | 10/2007 | Middlesworth |
| 2007/0237924 A1 | 10/2007 | Bruce |
| 2007/0249254 A1 | 10/2007 | Mansfield |
| 2007/0254176 A1 | 11/2007 | Patel |
| 2007/0254547 A1 | 11/2007 | Ducauchuis |
| 2007/0287983 A1 | 12/2007 | Lodge et al. |
| 2008/0003910 A1 | 1/2008 | Hughes |
| 2008/0003911 A1 | 1/2008 | Sabbagh |
| 2008/0045917 A1 | 2/2008 | Autran |
| 2008/0051748 A1 | 2/2008 | Black |
| 2008/0076315 A1 | 3/2008 | Mccormack |
| 2008/0114325 A1 | 5/2008 | Edwall et al. |
| 2008/0119102 A1 | 5/2008 | Hughes |
| 2008/0147031 A1 | 6/2008 | Long et al. |
| 2008/0241476 A1 | 10/2008 | Olguin |
| 2008/0305298 A1 | 12/2008 | Lakshmi |
| 2008/0312622 A1 | 12/2008 | Hundorf |
| 2009/0035527 A1 | 2/2009 | Kobayashi |
| 2009/0069772 A1 | 3/2009 | Sauer |
| 2009/0069778 A1 | 3/2009 | Sauer |
| 2009/0191779 A1 | 7/2009 | Cree |
| 2009/0240222 A1 | 9/2009 | Tomoko |
| 2009/0258210 A1 | 10/2009 | Iyad |
| 2009/0275909 A1 | 11/2009 | Sakaguchi |
| 2009/0292266 A1 | 11/2009 | Bäck |
| 2009/0294044 A1 | 12/2009 | Gill |
| 2009/0299318 A1 | 12/2009 | Faulks |
| 2009/0299322 A1 | 12/2009 | Faulks |
| 2009/0325447 A1 | 12/2009 | Austin |
| 2009/0325448 A1 | 12/2009 | Welch |
| 2009/0326503 A1 | 12/2009 | Lakso |
| 2010/0040826 A1 | 2/2010 | Mansfield et al. |
| 2010/0062231 A1 | 3/2010 | Abed |
| 2010/0076390 A1 | 3/2010 | Norrby |
| 2010/0090363 A1 | 4/2010 | Larsen |
| 2010/0104830 A1 | 4/2010 | Jaeger |
| 2010/0112313 A1 | 5/2010 | Nakakado |
| 2010/0168704 A1 | 7/2010 | Thomas |
| 2010/0222761 A1 | 9/2010 | Westwood et al. |
| 2010/0262105 A1 | 10/2010 | Turner |
| 2010/0262107 A1 | 10/2010 | Turner et al. |
| 2010/0268183 A1 | 10/2010 | Een |
| 2010/0280481 A1 | 11/2010 | Kline |
| 2010/0280484 A1 | 11/2010 | Kline et al. |
| 2010/0285286 A1 | 11/2010 | Middlesworth |
| 2011/0004176 A1 | 1/2011 | Andersson |
| 2011/0040273 A1 | 2/2011 | Sablone |
| 2011/0046594 A1 | 2/2011 | Sablone |
| 2011/0139657 A1 | 6/2011 | Hird et al. |
| 2011/0139658 A1 | 6/2011 | Hird et al. |
| 2011/0139659 A1 | 6/2011 | Hird et al. |
| 2011/0144610 A1 | 6/2011 | Karlson |
| 2011/0151739 A1 | 6/2011 | Bosler |
| 2011/0152812 A1 | 6/2011 | Hird et al. |
| 2011/0178490 A1 | 7/2011 | Lavon |
| 2011/0196332 A1 | 8/2011 | Cheng |
| 2011/0318987 A1 | 12/2011 | Ooishi |
| 2012/0022490 A1 | 1/2012 | Marche et al. |
| 2012/0045620 A1 | 2/2012 | Oba |
| 2012/0055613 A1 | 3/2012 | Baeck |
| 2012/0055615 A1 | 3/2012 | Baeck |
| 2012/0061015 A1 | 3/2012 | Lavon et al. |
| 2012/0061016 A1 | 3/2012 | Lavon et al. |
| 2012/0095429 A1 | 4/2012 | Kobayashi |
| 2012/0100351 A1 | 4/2012 | Covelli |
| 2012/0116342 A1 | 5/2012 | Stjernholm |
| 2012/0141742 A1 | 6/2012 | Yamaguchi |
| 2012/0143165 A1 | 6/2012 | Macura |
| 2012/0168063 A1 | 7/2012 | Beuther |
| 2012/0196091 A1 | 8/2012 | Mizutani |
| 2012/0209230 A1 | 8/2012 | Mansfield |
| 2012/0238980 A1 | 9/2012 | Lam |
| 2012/0251771 A1 | 10/2012 | Wilson |
| 2012/0252716 A1 | 10/2012 | Barnabas et al. |
| 2012/0277713 A1 | 11/2012 | Raycheck |
| 2012/0316526 A1 | 12/2012 | Rosati et al. |
| 2012/0321839 A1 | 12/2012 | Uematsu |
| 2013/0017370 A1 | 1/2013 | Yamaguchi |
| 2013/0022784 A1 | 1/2013 | Uematsu |
| 2013/0072887 A1 | 3/2013 | Lavon |
| 2013/0082418 A1 | 4/2013 | Curro et al. |
| 2013/0090623 A1 | 4/2013 | Ohashi |
| 2013/0095279 A1 | 4/2013 | Hauschildt |
| 2013/0144245 A1 | 6/2013 | Roe |
| 2013/0158497 A1 | 6/2013 | Yamaguchi |
| 2013/0164480 A1 | 6/2013 | Sakurai |
| 2013/0165883 A1 | 6/2013 | Kimura |
| 2013/0178815 A1 | 7/2013 | Ohashi |
| 2013/0184665 A1 | 7/2013 | Kato |
| 2013/0211356 A1 | 8/2013 | Nishikawa et al. |
| 2013/0213547 A1 | 8/2013 | Schneider et al. |
| 2013/0218116 A1 | 8/2013 | Schneider |
| 2013/0230700 A1 | 9/2013 | Schoenbeck |
| 2013/0236700 A1 | 9/2013 | Yamanaka |
| 2013/0255861 A1 | 10/2013 | Schneider |
| 2013/0255862 A1 | 10/2013 | Schneider et al. |
| 2013/0255863 A1 | 10/2013 | LaVon et al. |
| 2013/0255864 A1 | 10/2013 | Schneider et al. |
| 2013/0255865 A1 | 10/2013 | Brown et al. |
| 2013/0280481 A1 | 10/2013 | Mitsuno |
| 2013/0284850 A1 | 10/2013 | Lenser |
| 2013/0306226 A1 | 11/2013 | Zink |
| 2014/0005628 A1 | 1/2014 | Lavon et al. |
| 2014/0018222 A1 | 1/2014 | Sablone |
| 2014/0018759 A1 | 1/2014 | Yayasinghe et al. |
| 2014/0039434 A1 | 2/2014 | Xu |
| 2014/0041786 A1 | 2/2014 | Henke |
| 2014/0135194 A1 | 5/2014 | Sablone |
| 2014/0148774 A1 | 5/2014 | Brown |
| 2014/0163500 A1 | 6/2014 | Roe |
| 2014/0163506 A1 | 6/2014 | Roe |
| 2014/0163511 A1 | 6/2014 | Roe et al. |
| 2014/0234575 A1 | 8/2014 | Mitsuno et al. |
| 2014/0276525 A1 | 9/2014 | Lavon et al. |
| 2014/0330232 A1 | 11/2014 | Schönbeck |
| 2014/0367032 A1 | 12/2014 | Homoelle et al. |
| 2014/0377506 A1 | 12/2014 | Eckstein et al. |
| 2014/0377513 A1 | 12/2014 | Galie |
| 2014/0378924 A1 | 12/2014 | Turner |
| 2015/0032078 A1 | 1/2015 | Collins |
| 2015/0038929 A1 | 2/2015 | Van Malderen |
| 2015/0057630 A1 | 2/2015 | Tange |
| 2015/0126955 A1 | 5/2015 | Sauer |
| 2015/0147530 A1 | 5/2015 | Mitsuno |
| 2015/0147539 A1 | 5/2015 | Thomas |
| 2015/0164699 A1 | 6/2015 | Schmitz |
| 2015/0164705 A1 | 6/2015 | Thomas |
| 2015/0173961 A1 | 6/2015 | Powell et al. |
| 2015/0202091 A1 | 7/2015 | Sablone |
| 2015/0297419 A1 | 10/2015 | Nelson |
| 2015/0297421 A1 | 10/2015 | Nelson |
| 2015/0313774 A1 | 11/2015 | Homoelle |
| 2016/0008184 A1 | 1/2016 | Raycheck et al. |
| 2016/0013614 A1 | 1/2016 | Moto |
| 2016/0100999 A1 | 4/2016 | Hamilton |
| 2016/0136014 A1 | 5/2016 | Arora |
| 2016/0167334 A1 | 6/2016 | Arora |
| 2016/0206485 A1 | 7/2016 | Seitz |

(56) References Cited

U.S. PATENT DOCUMENTS

| | | |
|---|---|---|
| 2016/0270972 A1 | 9/2016 | Surushe |
| 2016/0324697 A1 | 11/2016 | Schoenbeck |
| 2017/0022339 A1 | 1/2017 | Hanschen et al. |
| 2017/0027775 A1 | 2/2017 | Barnes |
| 2017/0056256 A1 | 3/2017 | Smith |
| 2017/0071800 A1 | 3/2017 | Schonbeck |
| 2017/0079851 A1 | 3/2017 | Greening, II |
| 2017/0079854 A1 | 3/2017 | Butler |
| 2017/0087029 A1 | 3/2017 | Nelson |
| 2017/0142806 A1 | 5/2017 | Park |
| 2017/0252229 A1 | 9/2017 | Bonelli |
| 2017/0296399 A1* | 10/2017 | Kline ............... B32B 7/12 |
| 2017/0335498 A1 | 11/2017 | Hansen |
| 2018/0014979 A1 | 1/2018 | Fujita |
| 2018/0015709 A1 | 1/2018 | Takeuchi |
| 2018/0042777 A1 | 2/2018 | Dalal et al. |
| 2018/0042778 A1 | 2/2018 | Lenser |
| 2018/0042779 A1 | 2/2018 | Lenser |
| 2018/0042780 A1 | 2/2018 | Lenser |
| 2018/0042784 A1 | 2/2018 | Koshijima |
| 2018/0042785 A1 | 2/2018 | Dalal |
| 2018/0042786 A1 | 2/2018 | Mueller |
| 2018/0042787 A1 | 2/2018 | Lenser et al. |
| 2018/0271716 A1 | 9/2018 | Dalal |
| 2018/0271717 A1 | 9/2018 | Dria |
| 2018/0281296 A1 | 10/2018 | Uchida |
| 2019/0046363 A1 | 2/2019 | Lenser |
| 2019/0083323 A1 | 3/2019 | Sakai |
| 2019/0110936 A1 | 4/2019 | Becker |
| 2019/0125597 A1 | 5/2019 | Sauer et al. |
| 2020/0046576 A1 | 2/2020 | Schonbeck |
| 2020/0170846 A1 | 6/2020 | Lenser |
| 2020/0179179 A1 | 6/2020 | Lenser |
| 2020/0214363 A1 | 7/2020 | Sakai |
| 2020/0214904 A1 | 7/2020 | Tsunoda et al. |
| 2020/0268563 A1 | 8/2020 | Lenser |
| 2020/0397625 A1 | 12/2020 | Sakai |
| 2021/0077315 A1 | 3/2021 | Schönbeck et al. |
| 2021/0077316 A1 | 3/2021 | Schönbeck et al. |
| 2021/0077317 A1 | 3/2021 | Schönbeck et al. |
| 2021/0085532 A1 | 3/2021 | Lenser et al. |
| 2021/0186769 A1 | 6/2021 | Lenser et al. |
| 2021/0186770 A1 | 6/2021 | Lenser et al. |
| 2021/0307970 A1 | 10/2021 | Lenser et al. |
| 2021/0330514 A1 | 10/2021 | Lenser et al. |
| 2021/0378885 A1 | 12/2021 | Greening et al. |
| 2021/0393453 A1 | 12/2021 | Schönbeck et al. |
| 2022/0287887 A1 | 9/2022 | Lenser et al. |

FOREIGN PATENT DOCUMENTS

| | | |
|---|---|---|
| CN | 104703567 A | 6/2015 |
| CN | 104797228 A | 7/2015 |
| CN | 103434239 B | 11/2015 |
| CN | 204909840 U | 12/2015 |
| CN | 104837455 B | 4/2018 |
| CN | 108601686 A | 9/2018 |
| EP | 0666308 A2 | 8/1995 |
| EP | 1256594 A1 | 11/2002 |
| EP | 1447066 A1 | 8/2004 |
| EP | 2100575 A2 | 9/2009 |
| EP | 1263580 B1 | 9/2010 |
| EP | 1990188 B1 | 10/2012 |
| EP | 2891480 A1 | 7/2015 |
| EP | 2841364 B1 | 8/2016 |
| EP | 3170884 A1 | 5/2017 |
| EP | 3246443 A1 | 11/2017 |
| EP | 2647360 B1 | 6/2018 |
| EP | 3639801 A1 | 4/2020 |
| EP | 3251642 B1 | 8/2020 |
| JP | 2004223238 A | 8/2004 |
| JP | 2007521036 A | 8/2007 |
| JP | 2011139843 A | 7/2011 |
| JP | 5036641 B2 | 7/2012 |
| JP | 2012524645 A | 10/2012 |
| JP | 6240733 B1 | 11/2017 |
| JP | 2017065142 A | 11/2018 |
| JP | 4934835 B2 | 3/2021 |
| WO | 9115365 A1 | 10/1991 |
| WO | 9510996 A1 | 4/1995 |
| WO | 95010996 A1 | 4/1995 |
| WO | 9511652 A1 | 5/1995 |
| WO | 9516746 A1 | 6/1995 |
| WO | 9828123 A1 | 7/1998 |
| WO | 9919449 A1 | 4/1999 |
| WO | 2000045763 A1 | 8/2000 |
| WO | 2000059430 A1 | 10/2000 |
| WO | 0073031 A1 | 12/2000 |
| WO | 2002067809 A2 | 9/2002 |
| WO | 2003007864 A1 | 1/2003 |
| WO | 2004017882 A2 | 3/2004 |
| WO | 2004017885 A1 | 3/2004 |
| WO | 2004041990 A1 | 5/2004 |
| WO | 2004060652 A1 | 7/2004 |
| WO | WO 2006/020690 * | 8/2004 |
| WO | 2006124337 A1 | 11/2006 |
| WO | 2006138725 A2 | 12/2006 |
| WO | 2007036907 A3 | 4/2007 |
| WO | 2008023291 A3 | 2/2008 |
| WO | 2008026106 A2 | 3/2008 |
| WO | 2008156075 A1 | 12/2008 |
| WO | 2009082277 A1 | 7/2009 |
| WO | 2009146307 A1 | 12/2009 |
| WO | 2010055699 A1 | 5/2010 |
| WO | 2010118214 A1 | 10/2010 |
| WO | 2010126415 A1 | 11/2010 |
| WO | 2011080643 A2 | 7/2011 |
| WO | 2011125893 A1 | 10/2011 |
| WO | 2012052172 A1 | 4/2012 |
| WO | 2012030571 A3 | 5/2012 |
| WO | 2012112501 A1 | 8/2012 |
| WO | 2012137553 A1 | 10/2012 |
| WO | 2012154318 A1 | 11/2012 |
| WO | 2013018846 A1 | 2/2013 |
| WO | 2013027390 A1 | 2/2013 |
| WO | 2013047890 A1 | 4/2013 |
| WO | 2013132403 A1 | 9/2013 |
| WO | 2013157365 A1 | 10/2013 |
| WO | 2013163141 A1 | 10/2013 |
| WO | 2014011839 A1 | 1/2014 |
| WO | 2015168032 A1 | 11/2015 |
| WO | 2015195467 A1 | 12/2015 |
| WO | 2015195468 A1 | 12/2015 |
| WO | 2016069269 A1 | 5/2016 |
| WO | 2016073713 A1 | 5/2016 |
| WO | 2016109514 A1 | 7/2016 |
| WO | 2018031841 A1 | 2/2018 |
| WO | 2018183315 A1 | 10/2018 |
| WO | 2016121979 A1 | 1/2019 |
| WO | 2019089689 A2 | 5/2019 |

OTHER PUBLICATIONS

All Office Actions; U.S. Appl. No. 17/195,679, filed Mar. 9, 2021.
All Office Actions, U.S. Appl. No. 15/674,561.
EP Application No. 17754982.1, Third Party Observation, dated Jun. 17, 2020, 9 pages.
International Search Report, PCT/US2017/046398, dated Sep. 28, 2017, 13 pages.
All Office Actions; U.S. Appl. No. 17/720,363, filed Apr. 14, 2022.
U.S. Appl. No. 17/720,363, filed Apr. 14, 2022, to Todd Douglas Lenser.
Extended European Search Report and Search Opinion; Application No. 20183749.9; dated Nov. 9, 2020; 8 pages.
International Search Report and Written Opinion; Application No. PCT/US2020/070219; dated Oct. 1, 2020; 14 pages.
All Office Actions; U.S. Appl. No. 17/869,815, filed Jul. 21, 2022.
U.S. Appl. No. 17/869,815, filed Jul. 21, 2022, to Urmish Popatlal Dalal et al.
All Office Actions, U.S. Appl. No. 15/674,559.
All Office Actions, U.S. Appl. No. 15/674,563.
All Office Actions, U.S. Appl. No. 15/674,566.

(56) References Cited

OTHER PUBLICATIONS

All Office Actions, U.S. Appl. No. 15/674,575.
All Office Actions, U.S. Appl. No. 15/674,596.
All Office Actions, U.S. Appl. No. 15/674,625.
All Office Actions, U.S. Appl. No. 15/937,180.
All Ofice Actions, U.S. Appl. No. 15/937,235.
All Office Actions, U.S. Appl. No. 16/049,977.
All Office Actions, U.S. Appl. No. 16/741,819.
All Office Actions, U.S. Appl. No. 16/748,885.
Case 14424; PCT International Search Report, Appl. No. PCT/US2017/046388, dated Sep. 22, 2017, 15 pages.
Case 14445MQ; International Search Report, Appl. No. PCT/US2017/046397, dated Sep. 28, 2017, 13 pages.
Case 14525; PCT International Search Report and Written Opinion, Appl. No. PCT/US2017/046393, dated Sep. 25, 2017, 16 pages.
Case 14562Q; PCT International Search Report, Appl. No. PCT/US2017/046394, dated Sep. 28, 2017, 15 pages.
Case 14756M; International Search Report and Written Opinion, Appl. No. PCT/US2018/024549, dated May 30, 2018, 13 pages.
Case 14911; PCT International Search Report, Appl. No. PCT/US2017/046395, dated Sep. 20, 2017, 15 pages.
Case 14915Q; EP Application No. 17764961.3, Third Party Observation, dated Aug. 24, 2020, 6 pages.
Case 14915Q; International Search Report, Appl. No. PCT/US2017/049026, dated Oct. 19, 2017, 13 pages.
Case 15168; International Search Report, Appl. No. PCT/US2019/024011, dated Jul. 4, 2019, 14 pages.
All Office Actions; U.S. Appl. No. 18/485,494, filed Oct. 12, 2023.
U.S. Appl. No. 18/485,494, filed Oct. 12, 2023, to Todd Douglas Lenser ,et al.

* cited by examiner

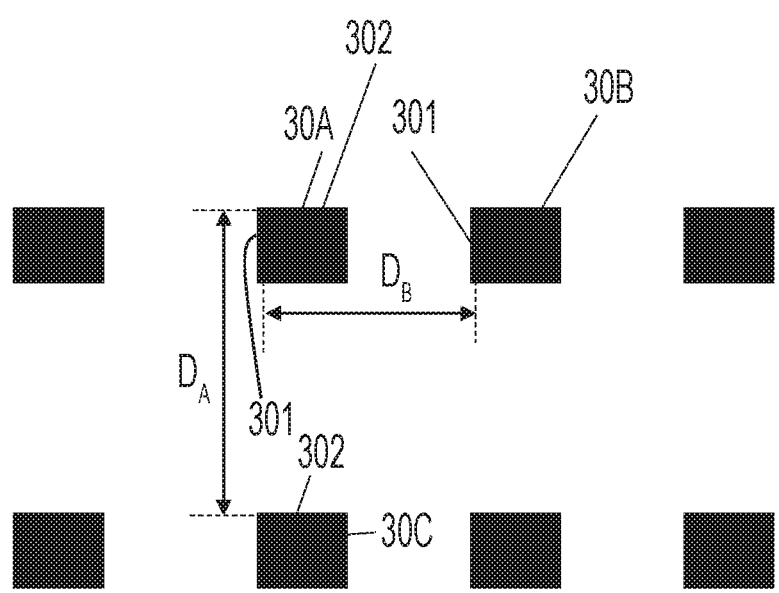
Fig. 10B

ABSORBENT ARTICLE WITH EAR PORTION

FIELD OF THE INVENTION

The present invention relates to absorbent articles having elastomeric portions, particularly absorbent articles having elastomeric ear portions.

BACKGROUND OF THE INVENTION

It has long been known that absorbent articles such as conventional absorbent articles (e.g., diapers, adult incontinence articles, feminine hygiene pads) offer the benefit of receiving and containing urine and/or other bodily exudates (e.g., feces, menses, mixture of feces and urine, mixture of menses and urine, etc.). To effectively contain bodily exudates, the article should provide a snug fit around the waist and legs of a wearer.

Manufacturers often use extensible areas, such as stretch side panels (i.e., ears), within the article to help achieve a snug fit. When worn, the stretch ears extend the article about the hip and waist of the wearer to anchor the product in use while still allowing the wearer to move comfortably. A fastening system is typically joined to the ear to further secure the product about the wearer. Stretch ears are typically laminates of coverstock materials (such as nonwovens) and elastomeric materials.

It has been proposed to create stretch laminates using ultrasonic bonding. In such instance, a stretched elastomeric material is combined with a nonwoven via ultrasonic bonding. After combination, the nonwoven will form corrugations when the laminate is in a relaxed state. These laminates can produce highly stretchable ears (depending on the level of stretch imparted in the elastomeric material) while avoiding the use of glues and mechanical activation. While ultrasonically bonded laminates may provide desirable stretch, they are known to provide less bond strength in some configurations. If the ears lack necessary strength, components of the ear and/or the entire ear laminate may tear or delaminate, a fastener may become detached from the ear, and/or the ear may detach from the rest of the article. Such failures render the article itself unusable. Thus, suitable high bond strength is necessary. Likewise, it is important to balance such strength with required extensibility and fit. In other words, the number and the positioning of bonds must not inhibit stretchability.

Therefore, there remains a need for laminates that provide both sufficient strength and sufficient extensibility. There is a continued need for stretch laminates having improved patterns that provide suitable strength to prevent delamination and/or tearing. Further, there is a continued need for patterns which provide high extensibility and permit easy extension for the end user. There is also a need for bond patterns that can be used to create desired properties in a cost effective and efficient manner.

SUMMARY OF THE INVENTION

The invention comprises the features of the independent claims herein. An absorbent article comprises a first waist region, a second waist region and a crotch region disposed between the first and second waist regions. The article also comprises a topsheet, a backsheet and an absorbent core disposed between the topsheet and the backsheet. The article further comprises a laminate. The laminate may be disposed in an ear and/or a waist feature in one of the first or second waist regions. The laminate comprises an elasticized region. The laminate comprises a first nonwoven, a second nonwoven and an elastomeric material sandwiched between said first and second nonwovens in the elasticized region. The laminate further comprises a bonding region comprising a bond density of at least 4% and at least partially overlapping the elastomeric material. In aspects of the invention, the laminate may comprise an Unload Force at 50% at least 0.90 N, an Average Peel Force of at least 70 gf/cm, an Elongation at 1.5 Load of 20% or greater and combinations thereof. Further, the laminate may comprise more than one bonding regions, where at least two regions comprise different bond densities.

BRIEF DESCRIPTION OF THE DRAWINGS

FIGS. 10A-10B are schematic plan views of exemplary bond patterns; and

DETAILED DESCRIPTION OF THE INVENTION

Figure 1:
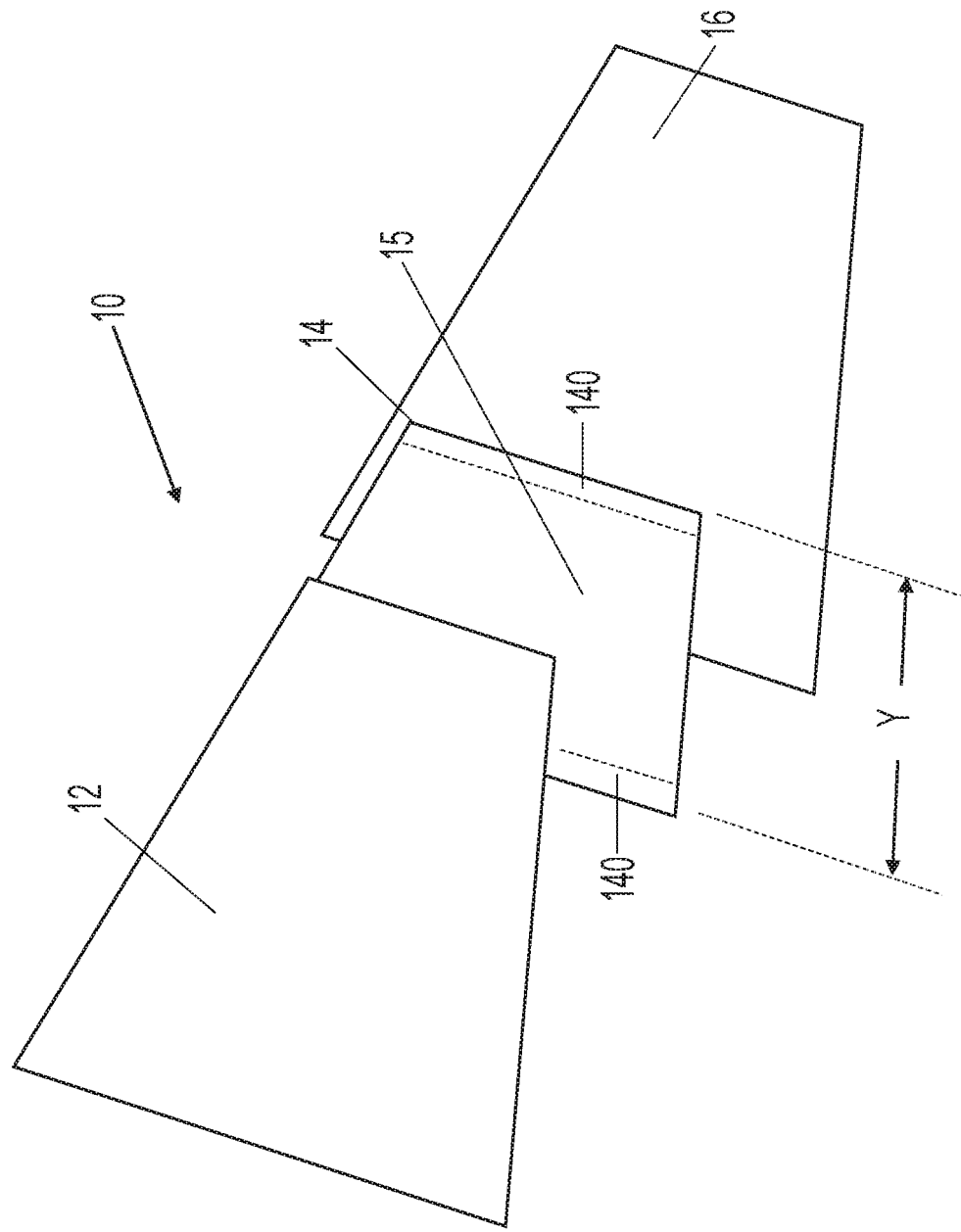
FIG. 1 is a schematic exploded view of a laminate in accordance with a nonlimiting embodiment of the present invention.

"Elastic," "elastomeric," and "elastically extensible" mean the ability of a material to stretch by at least 100% without rupture or breakage at a given load, and upon release of the load the elastic material or component exhibits at least 70% recovery (i.e., has less than 30% set) in one of the directions as per the Hysteresis Test described herein. Stretch, sometimes referred to as strain, percent strain, engineering strain, draw ratio, or elongation, along with recovery and set may each be determined according to the Hysteresis Test described in more detail below. Materials that are not elastic are referred as inelastic.

"Extensible" means the ability to stretch or elongate, without rupture or breakage, by at least 50% as per step 2 in the Hysteresis Test herein (replacing the specified 100% strain with 50% strain).

"Disposable," in reference to absorbent articles, means that the absorbent articles are generally not intended to be laundered or otherwise restored or reused as absorbent articles (i.e., they are intended to be discarded after a single use and, preferably, to be recycled, composted or otherwise discarded in an environmentally compatible manner).

"Absorbent article" refers to devices which absorb and contain body exudates and, more specifically, refers to devices which are placed against or in proximity to the body of the wearer to absorb and contain the various exudates discharged from the body. Exemplary absorbent articles include diapers, training pants, pull-on pant-type diapers (i.e., a diaper having a pre-formed waist opening and leg openings such as illustrated in U.S. Pat. No. 6,120,487), refastenable diapers or pant-type diapers, incontinence briefs and undergarments, diaper holders and liners, feminine hygiene garments such as panty liners, absorbent inserts, and the like.

"Grid" refers the arrangement of bonds, in an unstaggered manner, along a network of lines that cross each other to form a series of squares or rectangles. Bonds may be discrete or continuous.

"Disposed" refers to an element being located in a particular place or position.

"Joined" refers to configurations whereby an element is directly secured to another element by affixing the element directly to the other element and to configurations whereby an element is indirectly secured to another element by affixing the element to intermediate member(s) which in turn are affixed to the other element.

"Film" means a sheet-like material wherein the length and width of the material far exceed the thickness of the material (e.g., 10×, 50×, or even 1000× or more). Films are typically liquid impermeable but may be configured to be breathable.

"Laminate" means two or more materials that are bonded to one another by any suitable method known in the art (e.g., adhesive bonding, ultrasonic bonding, thermal bonding, or high pressure bonding using non-heated or heated patterned roll).

"Longitudinal" means a direction lengthwise in a component such that the longitudinal direction runs parallel to the maximum linear dimension in the x-y plane of the component. In an absorbent article as described herein, the longitudinal direction runs substantially perpendicular from a waist end edge to an opposing waist end edge when the absorbent article is in a flat out, uncontracted state, or from a waist end edge to the bottom of the crotch in a bifolded article.

"Lateral" refers to a direction generally perpendicular to the longitudinal direction. In the absorbent article described herein, the lateral direction runs substantially parallel from a side edge to an opposing side edge.

"Nonwoven" means a porous, fibrous material made from continuous (long) filaments (fibers) and/or discontinuous (short) filaments (fibers) by processes such as, for example, spunbonding, meltblowing, airlaying, carding, coforming, hydroentangling, and the like. Nonwovens do not have a woven or knitted filament pattern. Nonwovens may be liquid permeable or impermeable.

Figure 5:
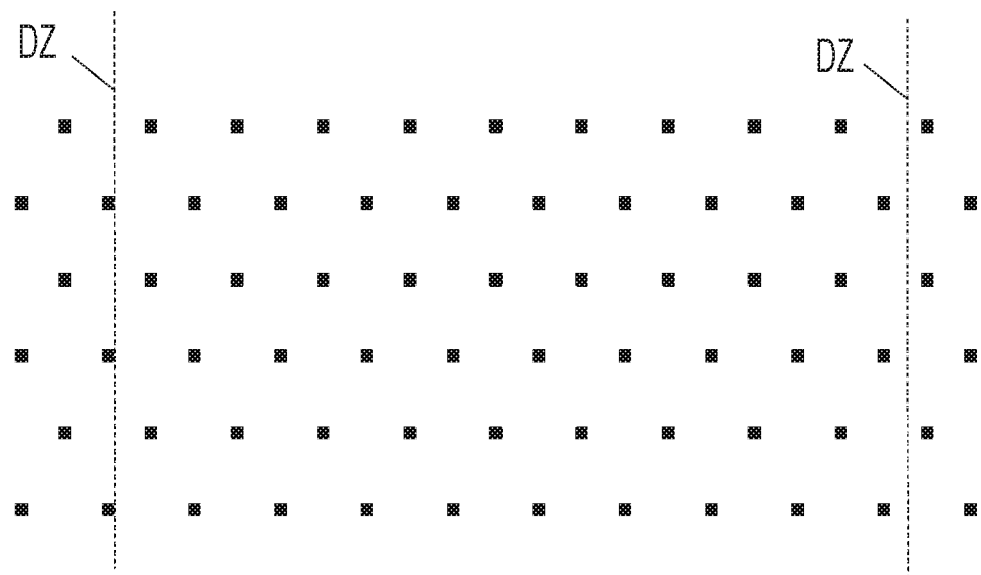
FIG. 5 is a schematic representation of a prior art bond pattern.

"Staggered" in relation to bonds refers to the arrangement of bonds in alternating positions, such that bonds in adjacent laterally-extending rows are offset by a lateral distance and/or bonds in adjacent longitudinally-extending columns are offset by a longitudinal distance as shown for example in FIG. 5.

"Relaxed" means the state of an element, material or component at rest with substantially no external force acting on the element, other than gravity.

Laminate

Figure 2:
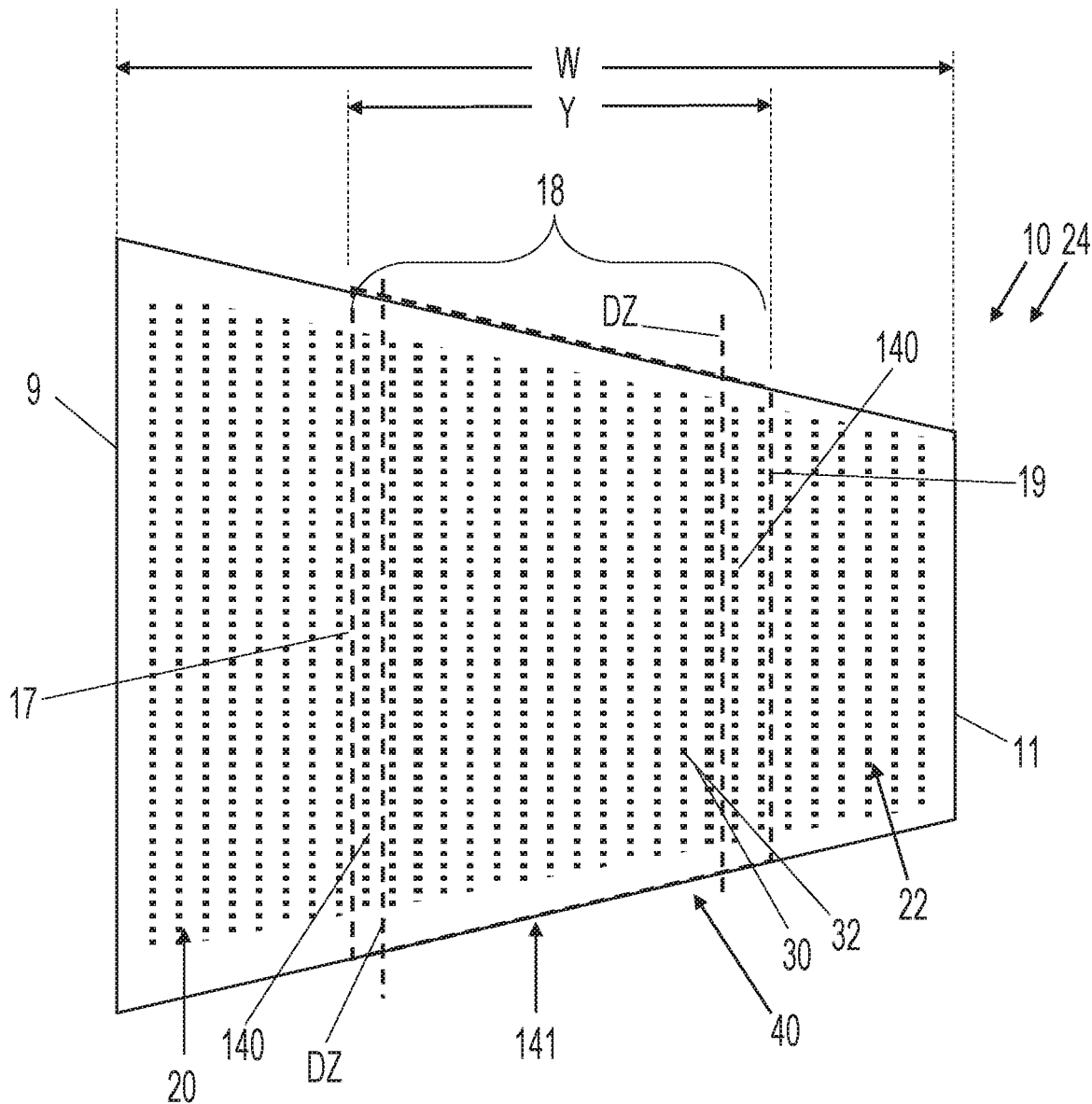
FIG. 2 is a schematic plan view of a laminate in accordance with a nonlimiting embodiment of the present invention.

As shown in FIG. 1, a laminate 10 comprises a first nonwoven 12 and an elastomeric layer 14. In various embodiments, the laminate comprises a second nonwoven 16, and the elastomeric layer 14 is sandwiched between the first and second nonwoven. Additional layers may be included (e.g., additional nonwovens, inelastic materials, elastic or extensible materials, etc.). In various embodiments, the laminate is elastomeric. One or more laminate layers are joined by a plurality of discrete bonds 30, which may comprise ultrasonic bonds 32 as illustrated in FIG. 2. The ultrasonic bonds may join the nonwoven layers through the elastomeric layer. The ultrasonically bonded laminate may be formed by the process and/or equipment disclosed in commonly assigned U.S. Patent App. Nos. 62/374,010, 62/419,515.

Any suitable nonwoven may be used in the laminate 10. Suitable nonwovens may comprise a basis weight of at least about 8 gsm, or about 30 gsm or less, or about 22 gsm or less, or about 17 gsm or less, or from about 10 gsm to about 22 gsm, reciting for said range every 1 gsm increment therein. Suitable nonwoven include but are not limited to spunbond, spunlaid, meltblown, air-through bonded, spunmelt, solvent-spun, electrospun, carded, film fibrillated, melt-film fibrillated, air-laid, dry-laid, wet-laid staple fibers, and other nonwoven web materials formed in part or in whole of polymer fibers, as known in the art. In nonlimiting examples, a nonwoven comprises a meltblown layer. Additionally, or alternatively, a nonwoven may comprise spunbond layers. In a nonlimiting example, a nonwoven comprises two or more spunbond layers. In further nonlimiting examples, one or more nonwovens may comprise a SMS configuration. Alternatively, one or more of the nonwovens in the ear may be void of meltblown layers. While meltblown layers have been found to enhance bonding in ears requiring adhesive (given the meltblown layer's inhibition of the adhesive's diffusion through the porous nonwoven structure), meltblown layers often lack strength. In some embodiments, a nonwoven consists essentially of spunbond layers. In some nonlimiting examples, both the first and the second nonwoven comprises at least 2 spunbond layers, or 3 or more spunbond layers.

The nonwoven web may be formed predominately of polymeric fibers. In some examples, suitable nonwoven fiber materials may include, but are not limited to polymeric materials such as polyolefins, polyesters, polyamide, or specifically, polypropylene (PP), polyethylene (PE), polylactic acid (PLA), polyethylene terephthalate (PET) and/or blends thereof. In some examples, the fibers may be formed of PP/PE blends such as described in U.S. Pat. No. 5,266,392. Nonwoven fibers may be formed of, or may include as additives or modifiers, components such as aliphatic polyesters, thermoplastic polysaccharides, or other biopolymers. Further useful nonwovens, fiber compositions, formations of fibers and nonwovens and related methods are described in U.S. Pat. Nos. 6,645,569; 6,863,933; and 7,112,621; and in U.S. patent application Ser. Nos. 10/338,603; 10/338,610; and Ser. No. 13/005,237.

The individual fibers of a nonwoven layer may be monocomponent or multicomponent (including bicomponent). The multicomponent fibers may be bicomponent, with differing polymeric components in, e.g., a core-and-sheath or side-by-side arrangement. The individual components may include polyolefins such as polypropylene or polyethylene, or their copolymers, or polyesters, thermoplastic polysaccharides or other biopolymers. Further, the nonwoven may include a blend of different fibers selected, for example from the types of polymeric fibers described above. In some examples, at least a portion of the fibers may exhibit a spiral curl which has a helical shape. According to one example, the fibers may include bicomponent fibers, which are individual fibers each including different materials, usually a first and a second polymeric material. It is believed that the use of side-by-side bi-component fibers is beneficial for imparting a spiral curl to the fibers. Examples of potentially suitable curled or "crimped" bicomponent fibers and nonwovens formed from them are described in U.S. Pat. Nos. 5,382,400; 5,418,045; 5,707,468; 6,454,989; 6,632,386; 5,622,772 and 7,291,239. For purposes herein, use of a nonwoven formed of crimped bicomponent or multicomponent fibers such as, for example, described in the patents and/or patent applications cited immediately above, may be desired as one or both nonwoven layers because they can feel particularly soft to the touch (for wearer comfort on the inside and aesthetically pleasing feel on the outside) and are generally quite pliable. In other nonlimiting examples, a nonwoven may be void of crimped fibers.

Where the laminate 10 comprises more than one nonwoven, the nonwovens may comprise the same basis weight or different basis weights. Likewise, the nonwovens may comprise the same layer configuration (e.g., SSS) or different layer configurations (e.g., SMS).

The elastomeric layer 14 comprises one or more elastomeric materials which provide elasticity to at least a portion of the layer 14. Nonlimiting examples of elastomeric materials include film (e.g., polyurethane films, films derived from rubber and/or other polymeric materials), an elastomeric coating applied to another substrate (e.g., a hot melt elastomer, an elastomeric adhesive, printed elastomer or elastomer co-extruded to another substrate), elastomeric nonwovens, scrims, and the like. Suitable elastomeric compositions comprise thermoplastic elastomers selected from the group consisting of styrenic block copolymers, polyesters, polyurethanes, polyether amides, and combinations thereof. Suitable styrenic block copolymers may be diblock, triblock, tetrablock, or other multi-block copolymers having at least one styrenic block. Exemplary styrenic block copolymers include styrene-butadiene-styrene, styrene-isoprene-styrene, styrene-ethylene/butylenes-styrene, styrene-ethylene/propylene-styrene, and the like. Commercially available styrenic block copolymers include KRATON (styrenic block copolymer; available from the Kraton Chemical Company, Houston, TX), SEPTON (styrenic block copolymer; available from Kuraray America, Inc., New York, NY), VECTOR (styrenic block copolymer; available from TSRC Dexco Chemical Company, Houston, TX) can be used. Additional suitable commercially available elastomers are ESTANE (polyurethane; available from Lubrizol, Inc, Ohio), PEBAX (polyether block amide; available from Arkema Chemicals, Philadelphia, PA), and HYTREL (polyester; available from DuPont, Wilmington, DE).

Semi-crystalline' or metallocene polyolefins are widely used in disposable absorbent products. It is known that their performance depends on amount of crystallinity. The crystallinity decreases with decreasing stereoregularity, and the material shows more elastic behavior. A number of methods are known for controlling crystallinity, such as by introducing stereo-irregularity or by introducing a co-monomer. Some homopolyolefins and random copolymers, as well as blends of such random copolymers, known by tradenames VISTAMAXX™ available from ExxonMobil and VERSIFY™ from Dow, are synthesized based on this principle, and tend to show elastic performance. The polyolefin elastomer materials useful herein include, but are not limited to, any polymers or copolymers of polyolefins such as polyethylene and polypropylene. Suitable examples of elastomeric polypropylenes include an elastic random poly(propylene/olefin) copolymer, an isotactic polypropylene containing stereo-irregularity, an isotactic/atactic polypropylene block copolymer, an isotactic polypropylene/random poly(propylene/olefin) copolymer block copolymer, a stereoblock elastomeric polypropylene, a syndiotactic polypropylene block poly(ethylene-co-propylene) block syndiotactic polypropylene triblock copolymer, an isotactic polypropylene block regioirregular polypropylene block isotactic polypropylene triblock copolymer, a polyethylene random (ethylene/olefin) copolymer block copolymer, a reactor blend polypropylene, a very low density polypropylene (or, equivalently, ultra low density polypropylene), a metallocene polypropylene, and blends or combinations thereof. Suitable polypropylene polymers including crystalline isotactic blocks and amorphous atactic blocks are described, for example, in U.S. Pat. Nos. 6,559,262, 6,518,378, and 6,169,151. Suitable isotactic polypropylene with stereo-irregularity along the polymer chain are described in U.S. Pat. No. 6,555,643 and EP 1 256 594 A1. Suitable examples include elastomeric random copolymers including propylene with a low level comonomer (e.g., ethylene or a higher alpha-olefin) incorporated into the backbone. Elastic polyethylene can be made similar to elastic polypropylene example and can be used to make elastic laminate of the present invention.

In some embodiments, two or more elastomers can be blended to achieve the desired elastic performance. For example, styrenic block copolymer can be blended with polyolefin-based elastomers, or polypropylene based elastomer can be blended with other polyolefin-based elastomers. The elastomer composition of the present invention may include one or more additives commonly used in the art to tailor the composition for a particular use.

In nonlimiting examples, the elastomeric layer 14 comprises a film 15. The film may comprise a single layer or multiple layers. The film may be extensible or may be elastic in the lateral direction and/or in the longitudinal direction. The film may be pre-activated prior to bonding, as disclosed, for example, in U.S. Pat. No. 9,533,067.

As shown in FIG. 2, the elastomeric layer may be shorter in one or more dimensions of the laminate than the laminate itself. For example, the elastomeric layer may comprise a first dimension, Y, and Y may be less than a dimension, W, of the laminate in the same direction by at least about 10 mm. In certain embodiments, Y is at least about 20% of, or from about 25% to about 100%, or from about 35% to about 85%, or about 80% or less of W, reciting for each range every 5% increment therein. Additionally, or alternatively, the elastomeric layer may have a dimension that is equal to one or more dimensions of the laminate. For example, the elastomeric layer may comprise substantially the same longitudinal length of the laminate throughout the lateral width of the elastomeric layer. In some embodiments, the elastomeric layer may have a basis weight of from about 5 to about 150 gsm, or from about 10 to about 100 gsm, or less than about 150 gsm, reciting for each range every 5 gsm increment therein.

The laminate 10 may comprise an elasticized region 18. The elasticized region 18 is generally defined by the perimeter of the elastomeric material 14. The elasticized region 18 may comprise a corrugated area 141, where the nonwoven layer(s) form gathers when the laminate is in a relaxed state as discussed below. The laminate may include a dead zone 140, which is a noncorrugated portion that includes the elastomeric layer. The dead zone 140 can be formed at one or more edges of the elastomeric layer 14, where said elastic layer was held during the laminate making process. For visualization in the figures, the dead zone is separated from the corrugated area by imaginary line DZ (which is not required to be a straight line). It is to be understood that noncorrugated means substantially free of corrugations; a small, negligible amount of corrugations may be present in the dead zone 140, which does not contribute to the overall functionality.

In the elasticized region 18, the laminate is elastically extensible. In some embodiments, the area of the elasticized region comprises at least about 20% of, or from about 30% to about 100%, or about 80% or less of the total area of the laminate, reciting for said range every 5% increment therein.

The laminate may further comprise one or more inelastic regions. In certain embodiments, the laminate 10 comprises a first inelastic region 20, which extends laterally outward from a first laminate edge 9 of the laminate to a first elastomeric material edge 17. The ear may further include a second inelastic region 22, which may extend laterally inward from a second laminate edge 11 to a second elastomeric material edge 19. The first and second inelastic regions may be made of the same material(s) or different materials.

In various embodiments, the laminate 10 comprises a gathered laminate 24, wherein one of the layers is strained to a greater degree than a remaining layer during lamination. In this way, the less extensible layer (i.e., the nonwoven 12, 16) will form gathers (i.e., corrugations) when the laminate 24 is in a relaxed state. In some embodiments, at least a portion of the elastomeric layer is strained while the nonwoven(s) are in a relaxed state during lamination. The elastomeric layer may be stretched one or more directions. Corrugations then form in the nonwoven layer(s) in the elasticized region when the subsequently formed laminate 24 is in a relaxed state. When making gathered laminates, the elastomeric layer is stretched in the stretch direction (i.e., the intended direction of stretch in the final product). The stretch direction may be lateral and/or longitudinal. In nonlimiting examples, the elastomeric layer is stretched in a direction corresponding with the lateral direction of the article. In other words, when the laminate is joined to the chassis subsequent to lamination, the laminate will be oriented such that the laminate is stretchable in the lateral direction of the article. As stated earlier, while forming the laminate, the elastomeric layer 14 may be fixed at one or more edges and stretched in other portions. Said fixed areas will become dead zones 140 in the assembled laminate.

As shown in FIG. 2 for example, two or more laminate layers are joined by one or more bonding regions 40. The bonding region comprises a plurality of discrete bonds 30, which may be ultrasonic bonds 32. The ultrasonic bonds may join the nonwoven layers through the elastomeric layer. The bonds may be rectangular or square. A discrete bond 30 may comprise a Discrete Bond Area of at least about 0.25 mm$^2$, or at least about 0.3 mm$^2$, or at least about 0.35 mm$^2$, or from about 0.2 mm$^2$ to about 2 mm$^2$, reciting for said range every 0.05 mm$^2$ increment therein, as determined by the Bond Dimensions Test Method Herein. Bond nubs used to create bonds may be at least about 0.25 mm$^2$, 0.36 mm$^2$, or at least about 0.49 mm$^2$, or at least about 0.5 mm$^2$, or from about 0.4 mm$^2$ to about 2 mm$^2$, reciting for said range every 0.05 mm$^2$.

Figure 3:
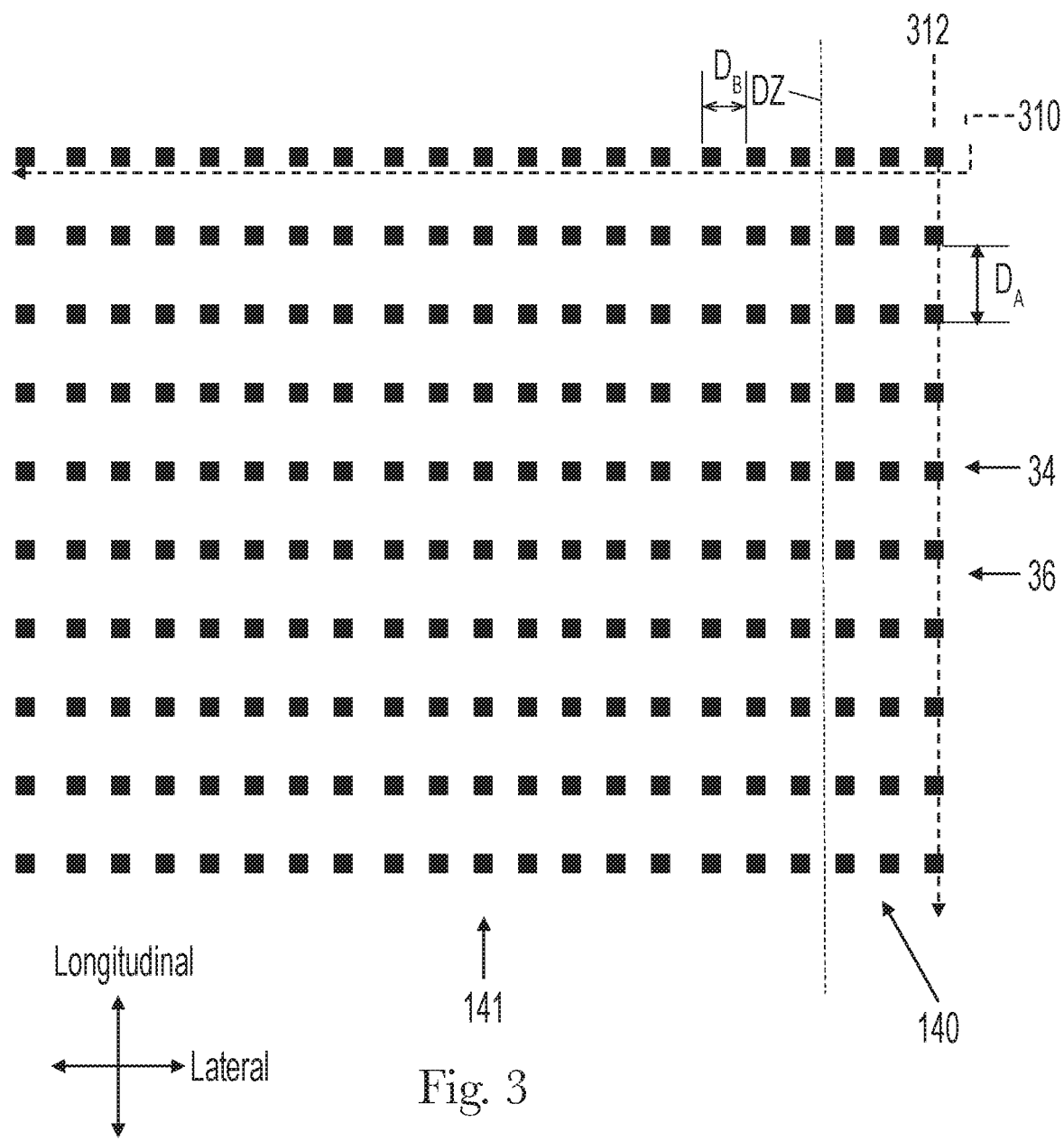
FIG. 3 is a schematic plan view of a bond pattern in accordance with a nonlimiting embodiment of the present invention.

The bonds may be arranged in a pattern 34. The pattern 34 may comprise a grid 36, having parallel rows 310 and parallel columns 312 as shown for example in FIG. 3. The rows may be substantially laterally-extending, and the columns may be substantially longitudinally-extending. Without being bound by theory, it is believed that arranging the bonds in a uniform pattern (as opposed to randomly positioned bonds) ensures suitable tensile strength as well as a desired stretch profile. In various nonlimiting examples, the pattern may be unstaggered as shown in FIGS. 2-3 for example. In other nonlimiting examples, the pattern may be staggered.

Bonds in adjacent extending rows may comprise a Maximum Longitudinal Separation Distance, $D_A$, of about 6 mm or less, or about 5 mm or less, or about 4 mm or less, or from about 2 mm to about 6 mm, reciting for said range every 0.1 mm increment therein. Bond in adjacent extending columns may comprise a Maximum Lateral Separation Distance, $D_B$, of about 4 mm or less, or about 3 mm or less, or about 2.5 mm or less, or from about 1.5 mm to about 2 mm, reciting for said range every 0.05 mm increment therein. The foregoing Separation Distances may be determined by the Bond Dimensions Test Method herein.

The bonding region 40 may comprise a Bond Density of at least about 2.5%, or at least about 3%, or at least about 4%, or at least about 4.25%, or from about 3% to about 6%, reciting for said range every 0.1% increment therein, as determined by the Bond Dimensions Test Method herein. Without being bound by theory, it is believed that the bond density values herein ensure suitable tensile strength, without significantly reducing the extensibility, more specifically the Extension at Peak Load, of the laminate. While increased bonding is known to counteract extensibility, the inventors have found that bonding regions arranged as taught herein do not significantly inhibit extensibility notwithstanding higher amounts of bonding.

Further to the above, even with high bond density, the laminate may comprise an Unload Force at 50% of at least about 0.9 N, or at least about 0.95 N, or at least about 1 N, or at least about 1.05 N, or from about 0.75 N to about 1.25 N, reciting for said range every 0.05 N increment therein, as determined by the Hysteresis Test Method herein. The laminate may comprise a % Force Relaxation of at least about 15%, or at least about 16%, or at least about 20%, or from about 15% to about 35%, reciting for said range every 1% increment therein, as determined by the Hysteresis Test Method herein.

Additionally, or alternatively, laminates of the present invention may comprise a Hysteresis Ratio of at least about 1.75, or at least about 2, or from about 1.5 to about 3, reciting for said range every 0.1 increment therein as determined by the Hysteresis Test Method herein. In this way, the laminate demonstrates high resilience. When incorporated into absorbent articles, laminates having Hysteresis Ratios of the present invention balance extensibility with strength. Laminates of the present invention permit ease of application while having sufficient ability to endure forces when worn (e.g., after application, stretch ears relax allowing the product to snuggly conform to the wearer).

The laminate, or more particularly the bonding region 40, may comprise an Elongation at 0.5N Load of at least about 5%, or at least about 5.5%, or at least about 5.75%, or at least about 5.8%, or from about 5% to about 6.5%, reciting for said range every 0.1% increment therein. The laminate, or more particularly the bonding region 40, may comprise an Elongation at 1.5N Load of at least about 20%, or at least about 21%, or at least about 25%, or at least about 26%, or from about 20% to about 30%, or from about 21% to about 28%, reciting for each range every 1% increment therein. The laminate, or more particularly the bonding region 40, may comprise an Elongation at 3.0N Load of at least about 100%, or at least about 105%, or at least about 110%, or at least about 115%, or from about 100% to about 130%, or from about 105% to about 125%, reciting for each range, every 1% increment therein. The laminate, or more particularly the bonding region 40, may comprise a Load at Peak of at least about 7 N/cm, or at least about 7.5 N/cm, or at least about 8 N/cm, or at least about 8.5 N/cm, or at least about 8.75 N/cm, or from about 7 N/cm to about 10 N/cm, or from about 7.5 N/cm to about 9.5 N/cm, or from about 8 N/cm to about 9 N/cm, reciting for each range every 0.5 N/cm increment therein. Additionally, or alternatively, the laminate, or more particularly the bonding region 40, may comprise an Elongation at Peak of at least about 250%, or at least about 300%, or at least about 325%, or at least about 350%, or at least about 375%, or at least about 400%, or from about 200% to about 400%, or from about 300% to about 400%, or from about 325% to about 390%, reciting for each range every 5% increment therein. Elongation and Load values may be determined by the Tensile Test Method herein. Without being bound by theory, it is believed that the foregoing Elongation and Load values, alone or in combination, indicate a high resistance to tearing.

Figure 4:
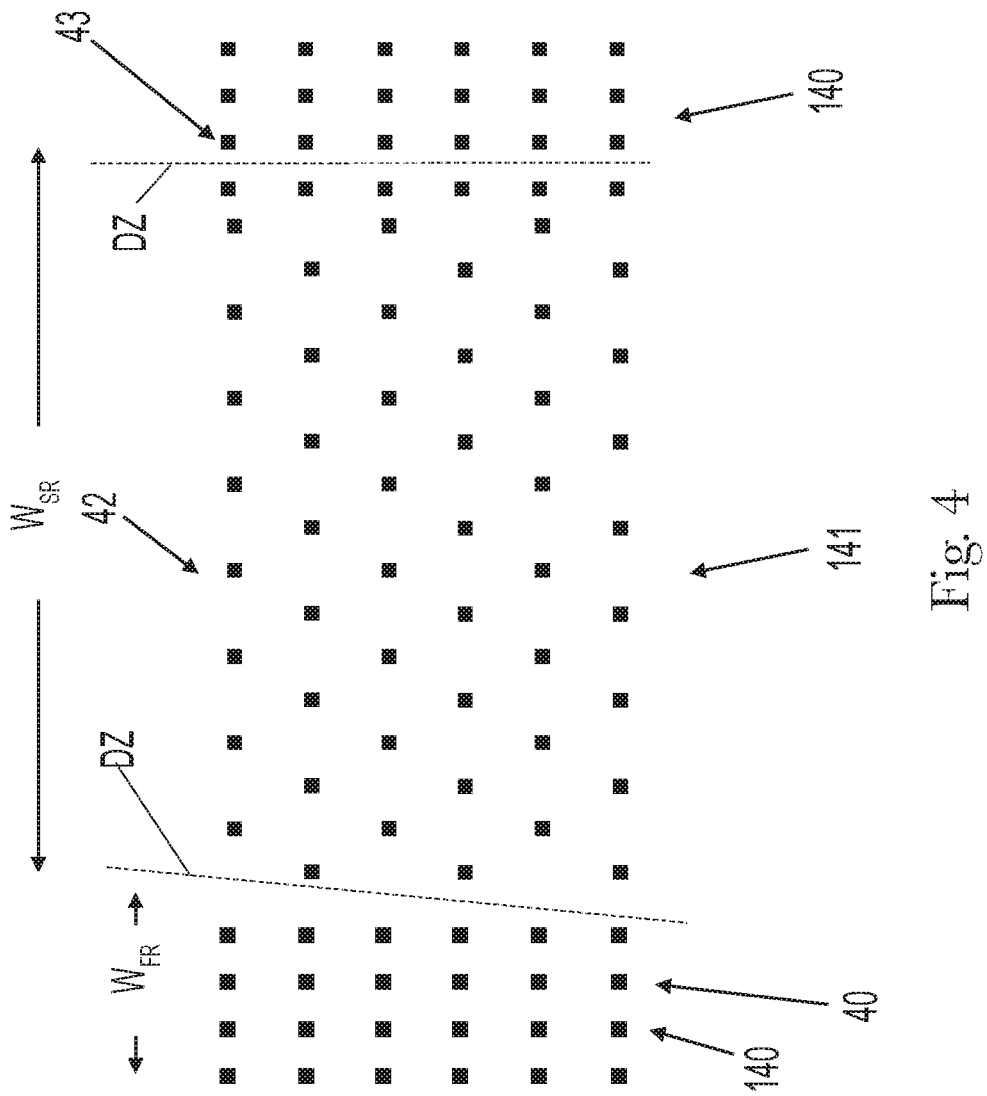
FIG. 4 is a schematic plan view of a bond pattern in accordance with a nonlimiting embodiment of the present invention.

In some embodiments, the laminate may comprise a second bonding region 42, as shown in FIG. 4. The second bonding region 42 may comprise a second bond density, which may differ from the first bond density. In nonlimiting examples, the second bond density is less than the first bond density. The second bond density may be at least about 30%, or at least about 40%, or at least about 45%, or at least about 50% or from about 20% to about 75%, or from about 30% to about 60%, or from about 40% to about 55% less than the first bond density, reciting for said ranges every 5% increment therein. For the avoidance of doubt, the calculation for determining the difference in bond density: [(first bond density−second bond density)/first bond density] *100%=difference in bond density.

The first and second bonding regions may each comprise an average region width as shown in FIG. 4. In some embodiments, the first region average width, $W_{FR}$, may be less than the second region average width, $W_{SR}$. In nonlimiting examples, the first region average width, $W_{FR}$, is at least about 10%, or at least about 20%, or at least about 25%, of at least about 30%, or from about 10% to about 70%, or from about 15% to about 60%, or from about 20% to about 50%, or from about 25% to about 45% of the second region average width, $W_{SR}$, reciting for said ranges every 1% increment therein. In this way, a laminate may be bonded with sufficient anchoring along one or more edges to ensure suitable strength and/or prevent film creep. In nonlimiting examples, the first bonding region may have a higher bond density and the region may extend across a dead zone and into an area of the laminate that is void, or substantially void of elastomeric material (i.e., an inelastic region 20 discussed above). The first bonding region may bridge the interface between the area of the laminate having the elastomeric layer and area of the laminate having just nonwoven layers. In some examples, the first region average width, WFR, may generally be equal distributed across the dead zone and across the inelastic region.

The second bonding region 42 may at least partially overlap the elasticized region 18. In nonlimiting examples, the second bonding region 42 at least partially overlaps the corrugated area 141 and the first bonding region at least partially overlaps a dead zone 140 as shown in FIG. 4. In such instances, the dead zone may be bonded by a denser bond pattern, which may prevent film creep. It is also contemplated that the second bonding region 42 may at least partially overlap a dead zone and/or the first bonding region may at least partially overlap the corrugated area. Any suitable configuration of bonding regions is within scope.

The second bonding region may differ from the first bonding region in bond density, pattern, Discrete Bond Area, bond type/material, bond shape, bond orientation or combinations thereof. In nonlimiting examples, the second bonding region 42 may be staggered, and the first bonding region 40 may comprise a grid pattern, as shown in FIG. 4.

The laminate may comprise a third bonding region 43, which may be the same as or different from the first or second bonding region.

Further to the above, the laminate may comprise an Average Peel Force of at least 50 gf/cm, or at least about 60 gf/cm, or at least about 70 gf/cm, or at least about 75 gf/cm, or at least about 90 gf/cm, or from about 30 gf/cm to about 100 gf/cm, or from about 45 gf/cm to about 95 gf/cm in a dead zone 140, reciting for each range every 5 gf/cm increment therein. The laminate may comprise an Average Peel Force of at least about 70 gf/cm, or at least about 75 gf/cm, or at least about 80 gf/cm, or at least about 100 gf/cm, or at least about 125 gf/cm, or at least about 130 gf/cm, or from about 70 gf/cm to about 150 gf/cm, or from about 75 gf/cm to about 135 gf/cm in the corrugated area, reciting for said ranges every 5 gf/cm increment therein. In particular, in a bonding region having a bond density of at least 5%, the Average Peel Force may be at least about 100 gf/cm, or at least about 125 gf/cm, or at least about 130 gf/cm, or from about 100 gf/cm to about 150 gf/cm, or from about 120 gf/cm to about 140 gf/cm, or from about 125 gf/cm to about 135 gf/cm, reciting for said ranges every 1 gf/cm increment therein. The Average Peel Force values may be determined by the Peel Force test method herein. Without being bound by theory, it is believed that patterns with the bond density values described herein provided better peel force because of the higher contact surface area of the bonds during peeling. In other words, the positioning, number and/or area of the bonds results in more surface area to be delaminated during peeling.

In certain embodiments, the elastomeric laminate 10 may comprise an Air Permeability Value of at least about 1 $m^3/m^2/min$, or from about 1 $m^3/m^2/min$ to about 125 $m^3/m^2/min$, or from about 1 $m^3/m^2/min$ to about 35 $m^3/m^2/min$ according to the Air Permeability Test Method herein, reciting for each range every 1 $m^3/m^2/min$ increment therein.

Without being bound by theory, it is believed that the bonding regions as taught above are particularly useful at high production speeds and volumes, including for example, line speeds of at least 200 m/min and/or bonding forces of at least 700 N.

Examples

The following laminate examples demonstrate properties of the invention herein. The four example laminates are used to illustrate the performance of gathered laminates comprising the three patterns in FIGS. 3, 4 and 5.

Example 1 comprises a first nonwoven and second nonwoven, and an elastomeric film sandwiched between the first and second nonwoven. Each of the first and second nonwoven are 17 gsm SMS available from Fibertex, Denmark under tradename B 10170AF. The elastomeric film is KG6707.130 available from Mondi, Germany and has a basis weight of 48 gsm. Prior to combining the film is ring-rolled activated. The film comprises a width of 43 mm in a relaxed condition. Said film was stretched to 195% strain (i.e., 28.5 mm stretched to about 84.3 mm, including a dead (unstretched) zone of about 7.25 mm on each side).

In its stretched state, the width grew by about 1.6 mm due to set. While the film was stretched as described, the first and second nonwoven were ultrasonically bonded through the film the using the bonding pattern shown in FIG. 4. In the corrugated area, the pattern is staggered, and the bond density is 2.02%. Further, $D_A$ is 4.65 mm and $D_B$ is 7.37 mm. In the dead zone, the pattern is a grid, the bond density is 4.25%, $D_A$ is 3.76 mm and $D_B$ is 2.14 mm. Each discrete bond was formed with a square nub having an area of 0.49 mm². Example 1 illustrates the structure and performance of the corrugated area in FIGS. 4 and 5. The dead zone in FIG. 4 is recreated in Example 3 to provide ample size for testing. The dead zone in FIG. 5 is recreated in Example 4 to provide ample size for testing.

Example 2 comprises a first nonwoven and second nonwoven, and an elastomeric film sandwiched between the first and second nonwoven. Each of the first and second nonwoven are 17 gsm SMS available from Fibertex, Denmark under tradename B 10170AF. The elastomeric film is KG6707.130 available from Mondi, Germany and has a basis weight of 48 gsm. Prior to combining, the film is ring-rolled activated. The film comprises a width of 44 mm in a relaxed condition. Said film was stretched to 216% strain (i.e., 26.5 mm stretched to about 84 mm, including a dead (unstretched) zone of about 8.75 mm on each side). In its stretched state, the width of the film grew by about 1.3 mm due to set. While the film was stretched as described, the first and second nonwoven were ultrasonically bonded through the film the using the bonding pattern shown in FIG. 3. The pattern is a grid, the bond density is 4.25%, $D_A$ is 3.76 mm and $D_B$ is 2.14 mm. Each discrete bond was formed with a square nub having an area of 0.49 mm². Example 2 illustrates the structure and performance of the corrugated area of FIG. 3. The dead zone in FIG. 3 is recreated in Example 3 to provide ample size for testing.

Example 3 comprises a first nonwoven and second nonwoven, and an elastomeric film sandwiched between the first and second nonwoven. Each of the first and second nonwoven are 17 gsm SMS available from Fibertex, Denmark under tradename B 10170AF. The elastomeric film is KG6707.140 available from Mondi, Germany and has a basis weight of 48 gsm. Prior to combining the film is ring-rolled activated. While the film was in relaxed condition as described, the first and second nonwoven were ultrasonically bonded through the film the using the bonding pattern shown in FIG. 3. The pattern is a grid, the bond density is 4.25%, $D_A$ is 3.76 mm and $D_B$ is 2.14 mm. Example 3 illustrates the structure and performance of the dead zones in FIGS. 3 and 4.

Example 4 comprises a first nonwoven and second nonwoven, and an elastomeric film sandwiched between the first and second nonwoven. Each of the first and second nonwoven are 17 gsm SMS available from Fibertex, Denmark under tradename B 10170AF. The elastomeric film is KG6707.130 available from Mondi, Germany and has a basis weight of 48 gsm. Prior to combining, the film is ring-rolled activated. The film comprises a width of 50 mm in a relaxed condition. While the film was in relaxed condition as described, the first and second nonwoven were ultrasonically bonded through the film the using the bonding pattern shown in FIG. 5. The pattern is staggered, and the bond density is 2.02%. Further, DA is 4.65 mm and $D_B$ is 7.37 mm. Example illustrates the structure and performance of the dead zone in FIG. 5.

Table 1 below summarizes the tested patterns and laminates from which the below data is derived.

TABLE 1

Laminates and Patterns

| Option | Example/Pattern Tested for Corrugated Area | Example/Pattern Tested for Dead Zone |
|---|---|---|
| Base (Prior Art) - FIG. 5 | Example 1 - Staggered Bond Density of 2.02% | Example 4 - Staggered Bond Density of 2.02% |
| Hybrid - FIG. 4 | Example 1 - Staggered Bond Density of 2.02.% | Example 3 - Grid, Bond Density of 4.25% |
| High Density - FIG. 3 | Example 2 - Grid, Bond Density of 4.25% | Example 3 - Grid, Bond Density of 4.25% |

Table 2 shows tensile values in the corrugated area for the three pattern options. As can be seen, the denser pattern exhibited better elongation under different levels of force.

TABLE 2

Tensile Data of Corrugated area

| | Bond Density in Elasticized Region % | Elongation at 0.5N Load % | Elongation at 1.5N Load % | Elongation at 3.0N Load % | Load at Peak N/cm | % Elongation At Peak % |
|---|---|---|---|---|---|---|
| Example 1 - Base Option and Hybrid Option | 2.02% | 5.00 | 20.14 | 103.59 | 7.93 | 329.50 |
| Example 1 - High Density Option | 4.25 | 5.80 | 26.45 | 119.14 | 8.79 | 365.12 |

Table 3 shows hysteresis values in the corrugated area for the three pattern options. As can be seen, the denser pattern shows substantially parity hysteresis performance to the lower density pattern, despite having an increased amount of bonding.

TABLE 3

Hysteresis of the Corrugated area

| | Load Force @ 75% N | Load Force @100% N | Unload Force @ 50% N | % Force Relaxation % | Hysteresis Ratio Unitless |
|---|---|---|---|---|---|
| Example 1 - Base Option and Hybrid Option | 2.21 | 2.51 | 1.08 | 17.22 | 2.05 |

TABLE 3-continued

Hysteresis of the Corrugated area

| | Load Force @ 75% N | Load Force @100% N | Unload Force @ 50% N | % Force Relaxation % | Hysteresis Ratio Unitless |
|---|---|---|---|---|---|
| Example 2 - High Density Option | 2.11 | 2.43 | 0.99 | 17.62 | 2.13 |

Table 4 shows Average Peel Force values in the corrugated area and in the dead zones for the three pattern options. As can be seen the denser pattern provides enhanced peel strength in both the corrugated area and the dead zones. Not only does this reduce delamination and tearing, but the enhanced peel strength in the dead zones also reduces film creep during product use.

TABLE 4

Average Peel Force

| Option | Example/ Pattern in Corrugated Area | Average Peel Force in Corrugated area gf/cm | Example/ Pattern in Dead Zone | Average Peel Force in Dead Zone gf/cm |
|---|---|---|---|---|
| Base - FIG. 5 | Example 1 - Staggered Bond Density of 2.57% | 75.30 | Example 4 - Staggered Bond Density of 2.57% | 41.74 |
| Hybrid - FIG. 4 | Example 1 - Staggered Bond Density of 2.57% | 75.30 | Example 3 - Grid, Bond Density of 5.13% | 92.14 |
| High Density - FIG. 3 | Example 2 - Grid, Bond Density of 5.13% | 131.53 | Example 3 - Grid, Bond Density of 5.13% | 92.14 |

Article Comprising Laminate

A laminate 10 of the present invention may be incorporated into an absorbent article 100, such as a disposable absorbent article. The laminate may be attached to one or more layers of the chassis 120 by a chassis attachment bond 102. The chassis attachment bond may comprise ultrasonic bonds, adhesive bonds, mechanical bonds or combinations thereof.

Figure 6:
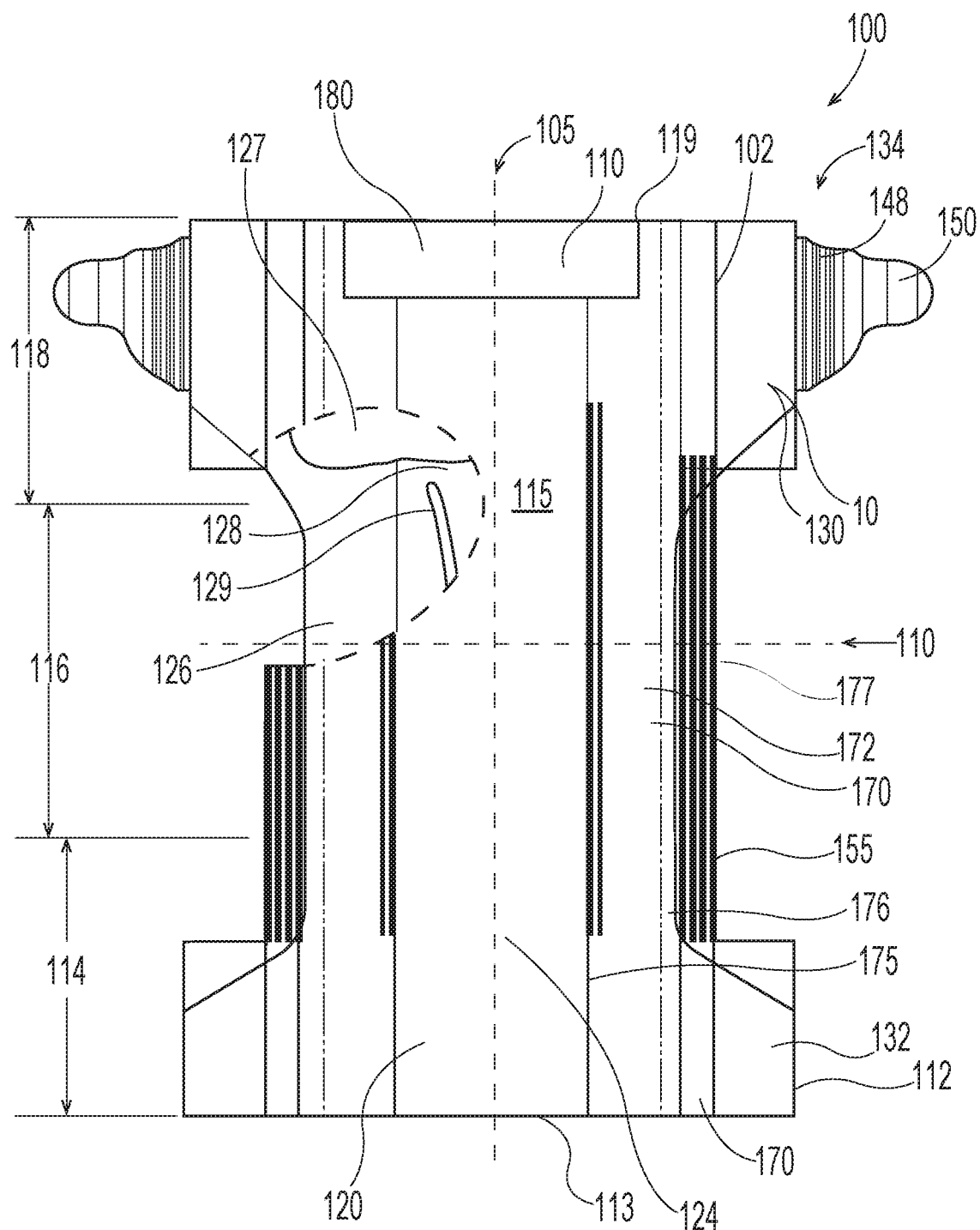
FIG. 6 is a schematic plan view of an exemplary absorbent article according to a nonlimiting embodiment of the present invention. The absorbent article is shown in a flat, uncontracted state.

FIG. 6 is a plan view of an exemplary, non-limiting embodiment of an absorbent article 100 of the present invention in a flat, uncontracted state. The body-facing surface 115 of the absorbent article 100 is facing the viewer. The absorbent article 100 includes a longitudinal centerline 105 and a lateral centerline 110.

The absorbent article 100 comprises a chassis 120. The absorbent article 100 and chassis 120 are shown to have a first waist region 114, a second waist region 118 opposed to the first waist region 114, and a crotch region 116 located between the first waist region 114 and the second waist region 118. The waist regions 114 and 118 generally comprise those portions of the absorbent article which, when worn, encircle the waist of the wearer. The waist regions 114 and 118 may include elastic members 155 such that they gather about the waist of the wearer to provide improved fit and containment. The crotch region 116 is the portion of the absorbent article which, when the absorbent article is worn, is generally positioned between the legs of the wearer.

The outer periphery of the chassis 120 is defined by longitudinal edges 112 and waist edges (first waist edge 113 in first waist region 114 and second waist edge 119 in second waist region 118). The chassis 120 may have opposing longitudinal edges 112 that are oriented generally parallel to the longitudinal centerline 105. However, for better fit, longitudinal edges 112 may be curved or angled to produce, for example, an "hourglass" shape article when viewed in a plan view as shown in FIG. 6. The chassis 120 may have opposing lateral edges 113, 119 (i.e., the first waist edge 113 and second waist edge 119) that are oriented generally parallel to the lateral centerline 110.

The chassis 120 may comprise a liquid permeable topsheet 124, a backsheet 126, and an absorbent core 128 between the topsheet 124 and the backsheet 126. The topsheet 124 may be joined to the core 128 and/or the backsheet 126. The backsheet 126 may be joined to the core 128 and/or the topsheet 124. It should be recognized that other structures, elements, or substrates may be positioned between the core 128 and the topsheet 124 and/or backsheet 126. In some embodiments, an acquisition-distribution system 127 is disposed between the topsheet 126 and the absorbent core 128.

In certain embodiments, the chassis 120 comprises the main structure of the absorbent article 100 with other features added to form the composite absorbent article structure. While the topsheet 124, the backsheet 126, and the absorbent core 128 may be assembled in a variety of well-known configurations, absorbent article configurations are described generally in U.S. Pat. Nos. 3,860,003; 5,151,092; 5,221,274; 5,554,145; 5,569,234; 5,580,411; and 6,004,306.

Components of the disposable absorbent article can at least partially be comprised of bio-sourced content as described in U.S. Pat. Pub. Nos. 2007/0219521A1, 2011/0139658A1, 2011/0139657A1, 2011/0152812A1, and 2011/0139659A1. These components include, but are not limited to, topsheets, backsheet films, backsheet nonwovens, ears/ear laminates, leg gasketing systems, superabsorbent, acquisition layers, core wrap materials, adhesives, fastener systems, and landing zones. In at least one embodiment, a disposable absorbent article component comprises a bio-based content value from about 10% to about 100%, or from about 25% to about 75%, or from about 50% to about 60% using ASTM D6866-10, method B. In order to apply the methodology of ASTM D6866-10 to determine the bio-based content of any component, a representative sample of the component must be obtained for testing. In at least one embodiment, the disposable absorbent article component can be ground into particulates less than about 20 mesh using known grinding methods (e.g., WILEY® mill), and a representative sample of suitable mass taken from the randomly mixed particles.

One or more masking layers or materials may be provided in the absorbent article 100. A masking layer may be a layer that provides a cushiony feel when the absorbent article is touched from the garment-facing surface or the wearer-facing surface. The masking layer may "mask" a grainy feel potentially caused by the absorbent material. The masking layer may "mask" bodily exudates from being visible when viewing the wearer-facing surface or the garment-facing surface. The masking layer may have a basis weight in the range of about 15 gsm to about 50 gsm or about 15 gsm to about 40 gsm. The masking layer may comprise one or more nonwoven materials (e.g., a hydroentangled nonwoven material), foams, pulp layers, and/or other suitable materials. The masking layer may be the outer cover material of the backsheet. The masking layer may be the layer forming the garment-facing side or the wearer-facing side of the core wrap. The masking layer may be a separate material positioned intermediate the garment-facing side of the core and the liquid impermeable backsheet.

The laminate 10 of the present invention forms or is a portion of one or more components of the article, including but not limited to the ear, waist features, belts and combinations thereof.

Topsheet:

The topsheet 124 is generally a portion of the absorbent article 100 that may be positioned at least in partial contact or close proximity to a wearer. Suitable topsheets 124 may be manufactured from a wide range of materials, such as porous foams; reticulated foams; apertured plastic films; or woven or nonwoven webs of natural fibers (e.g., wood or cotton fibers), synthetic fibers (e.g., polyester or polypropylene fibers), or a combination of natural and synthetic fibers. The topsheet 124 is generally supple, soft feeling, and non-irritating to a wearer's skin. Generally, at least a portion of the topsheet 124 is liquid pervious, permitting liquid to readily penetrate through the thickness of the topsheet 124. The topsheet 124 may be apertured. The topsheet may be apertured by overbonding a material and then rupturing the overbonds through ring rolling, such as disclosed in U.S. Pat. No. 5,628,097.

Any portion of the topsheet may be coated with a skin care composition, an antibacterial agent, a surfactant, and/or other beneficial agents. The topsheet may be hydrophilic or hydrophobic or may have hydrophilic and/or hydrophobic portions or layers. If the topsheet is hydrophobic, typically apertures will be present so that bodily exudates may pass through the topsheet.

Absorbent Core:

The absorbent core 128 may comprise a wide variety of liquid-absorbent materials commonly used in disposable diapers and other absorbent articles. Examples of suitable absorbent materials include comminuted wood pulp, which is generally referred to as air felt creped cellulose wadding; melt blown polymers, including co-form; chemically stiffened, modified or cross-linked cellulosic fibers; tissue, including tissue wraps and tissue laminates; absorbent foams; absorbent sponges; superabsorbent polymers; absorbent gelling materials; or any other known absorbent material or combinations of materials. In one embodiment, at least a portion of the absorbent core is substantially cellulose free and contains less than 10% by weight cellulosic fibers, less than 5% cellulosic fibers, less than 1% cellulosic fibers, no more than an immaterial amount of cellulosic fibers or no cellulosic fibers. It should be understood that an immaterial amount of cellulosic material does not materially affect at least one of the thinness, flexibility, and absorbency of the portion of the absorbent core that is substantially cellulose free. Among other benefits, it is believed that when at least a portion of the absorbent core is substantially cellulose free, this portion of the absorbent core is significantly thinner and more flexible than a similar absorbent core that includes more than 10% by weight of cellulosic fibers. The amount of absorbent material, such as absorbent particulate polymer material present in the absorbent core may vary, but in certain embodiments, is present in the absorbent core in an amount greater than about 80% by weight of the absorbent core, or greater than about 85% by weight of the absorbent core, or greater than about 90% by weight of the absorbent core, or greater than about 95% by weight of the core. In some embodiments, the absorbent core may comprise one or more channels 129, wherein said channels are substantially free of absorbent particulate polymer material. The channels 129 may extend longitudinally or laterally. The absorbent core may further comprise two or more channels. The channels may be straight, curvilinear, angled or any workable combination thereof. In nonlimiting examples, two channels are symmetrically disposed about the longitudinal axis.

Backsheet:

The backsheet 126 is generally positioned such that it may be at least a portion of the garment-facing surface of the absorbent article 100. The backsheet 126 may be joined to portions of the topsheet 124, the absorbent core 128, and/or any other layers of the absorbent article by any attachment methods known to those of skill in the art. Backsheet 126 may be designed to prevent the exudates absorbed by and contained within the absorbent article 100 from soiling articles that may contact the absorbent article 100, such as bed sheets and undergarments. In certain embodiments, the backsheet 126 is substantially water-impermeable. The backsheet may, for example, be or comprise a thin plastic film, such as a thermoplastic film having a thickness of about 0.012 mm to about 0.051 mm. Other suitable backsheet materials may include breathable materials which permit vapors to escape from the absorbent article, while still preventing, or at least inhibiting, bodily exudates from passing through the backsheet.

Backsheet 126 may also consist of more than one layer. The backsheet 126 may comprise an outer cover and an inner layer. The outer cover material may comprise a bond pattern, apertures, and/or three-dimensional features. The outer cover material may be a nonwoven material, such as a hydroentangled nonwoven material.

Ears/Fasteners:

The absorbent article 100 may include one or more ears 130, including for example front ears 132 disposed in the first waist region and/or back ears 134 disposed in the second waist region. The ears 130 may be integral with the chassis or discrete elements joined to the chassis 120 at a chassis attachment bond 102, which may join one or more layers of the ear to the chassis. The ears 130 may be extensible or elastic. The ears 130 may be formed from one or more nonwoven webs, woven webs, knitted fabrics, polymeric and elastomeric films, apertured films, sponges, foams, scrims, or combinations and/or laminates of any the foregoing.

In some embodiments, the ear 130 may include elastomers, such that the ear is stretchable. In certain embodiments, the ears 130 may be formed of a stretch laminate such as a nonwoven/elastomeric material laminate or a nonwoven/elastomeric material/nonwoven laminate, which also results in the ear being stretchable. The ear 120 may be extensible in the lateral direction of the article. In some embodiments, the ear is elastic in the lateral direction. In further embodiments, the ear 130 may extend more in the lateral direction than in the longitudinal direction. Alternatively, the ear may extend more in the longitudinal direction than in the lateral direction. In certain nonlimiting examples, the ear may include one or more inelastic regions along with a separate elastic region.

In some embodiments, the ear comprises a laminate of one or more nonwovens and one or more elastic materials, such as the laminate 10 having any of the features or laminate layers described herein with respect to laminates of the present invention.

Any suitable nonwoven may be used in an ear 130. Suitable nonwovens may comprise a basis weight of at least about 8 gsm, or less than about 22 gsm, or about 17 gsm or less, or from about 10 gsm to about 17 gsm, reciting for said range every 1 increment therein. Where the ear 130 comprises more than one nonwoven, the nonwovens may comprise the same basis weight or different basis weights. Likewise, the nonwovens may comprise the same layer structure or different layer structures. Further, a nonwoven in the ear may comprise the same or different features of nonwovens in the backsheet, topsheet, leg gasketing system and/or waist feature.

The ear may comprise an ultrasonically bonded ear as is disclosed for example in U.S. patent application Ser. No. 15/674,559. The ear may be a gathered laminate 24. Alternatively, the ear may be activated by processes disclosed in U.S. Pat. Pub. No. 2013/0082418, U.S. Pat. Nos. 5,167,897; 5,993,432; 5,156,793; 5,167,897; 7,062,983 and 6,843,134 for example.

The ear may be joined to the chassis at a chassis attachment bond 102. In some nonlimiting examples, the chassis attachment bond is located in an inelastic region of the ear.

The absorbent article 100 may also include a fastening system 148. When fastened, the fastening system 148 interconnects the first waist region 116 and the rear waist region 118 resulting in a waist circumference that may encircle the wearer during wear of the absorbent article 100. The fastening system 148 may comprise a fastening element 150 such as tape tabs, hook and loop fastening components, interlocking fasteners such as tabs & slots, buckles, buttons, snaps, and/or hermaphroditic fastening components, although any other known fastening means are generally acceptable. The absorbent article may further comprise a landing zone to which a fastening element can engage and/or a release tape that protects the fastening elements from insult prior to use. Some exemplary surface fastening systems are disclosed in U.S. Pat. Nos. 3,848,594; 4,662,875; 4,846,815; 4,894,060; 4,946,527; 5,151,092; and 5,221,274. An exemplary interlocking fastening system is disclosed in U.S. Pat. No. 6,432,098. In some embodiments, the fastening system 148 and/or the element 150 is foldable.

The fastening system 148 may be joined to any suitable portion of the article 100 by any suitable means. The fastening system may be joined to the ear between layers.

Leg Gasketing System

The absorbent article 100 may comprise a leg gasketing system 170 attached to the chassis 120, which may comprise one or more cuffs. The leg gasketing system may comprise a pair of barrier leg cuffs 172. Each barrier leg cuff may be formed by a piece of material which is bonded to the absorbent article so that it may extend upwards from a wearer-facing surface of the absorbent article and provide improved containment of fluids and other body exudates approximately at the junction of the torso and legs of the wearer. The barrier leg cuffs are delimited by a proximal edge joined directly or indirectly to the topsheet 124 and/or the backsheet 126 and a free terminal edge 175, which is intended to contact and form a seal with the wearer's skin. In some embodiments, the free terminal edge 175 comprises a folded edge. The barrier leg cuffs 172 extend at least partially between the front waist edge 113 and the rear waist edge 119 of the absorbent article on opposite sides of the longitudinal centerline 105 and are at least present in the crotch region. The barrier leg cuffs may be joined at the proximal edge with the chassis of the article by a bond which may be made by gluing, fusion bonding, or a combination of other suitable bonding processes.

The barrier leg cuffs may be integral with the topsheet 124 or the backsheet 126 or may be a separate material joined to the article's chassis. Each barrier leg cuff 172 may comprise one, two or more elastic elements 155 close to the free terminal edge 175 to provide a better seal.

In addition to the barrier leg cuffs 172, the article may comprise gasketing cuffs 176, which are joined to the chassis of the absorbent article, in particular to the topsheet 124 and/or the backsheet 126 and are placed externally relative to the barrier leg cuffs 172. The gasketing cuffs 176 may provide a better seal around the thighs of the wearer. A gasketing cuff may comprise a proximal edge and a free terminal edge 177. The free terminal edge 177 may comprise a folded edge. Each gasketing cuff may comprise one or more elastic elements 155 in the chassis of the absorbent article between the topsheet 124 and backsheet 126 in the area of the leg openings. All, or a portion of, the barrier leg cuffs and/or gasketing cuffs may be treated with a lotion or another skin care composition.

In further embodiments, the leg gasketing system comprises barrier leg cuffs that are integral with gasketing cuffs. Suitable leg gasketing systems which may be part of the absorbent article are disclosed in U.S. Pat. App. No. 62/134,622, Ser. No. 14/077,708; U.S. Pat. Nos. 8,939,957; 3,860,003; 7,435,243; 8,062,279.

Elastic Waist Feature

The absorbent article 100 may comprise at least one elastic waist feature 180 that helps to provide improved fit and containment, as shown in FIG. 6. The elastic waist feature 180 is generally intended to expand and contract to dynamically fit the wearer's waist. Elasticized waist features include waistbands, waist cuffs having pockets formed from a portion of the waist feature 180 that is unattached from the chassis 120, and waist panels designed to fit securely about the abdomen of the wearer. Nonlimiting examples of elasticized waist features are disclosed in U.S. patent application Ser. Nos. 13/490,543; 14/533,472; and 62/134,622. Waist features 180 may be joined to the chassis 120 in the first waist region 114 and/or in the second waist region 118. The waist feature can be used in conjunction with the ear 130 to provide desirable stretch and flexibility for proper fit of the article on the wearer. The waist feature may comprise a laminate 10 having any of the features described herein with respect to laminates. The waist feature may be extensible or elastic in the lateral and/or longitudinal directions. In some embodiment, the waist feature 180 comprises a belt 220.

Adult or Baby Pant Absorbent Articles

Figure 7A:
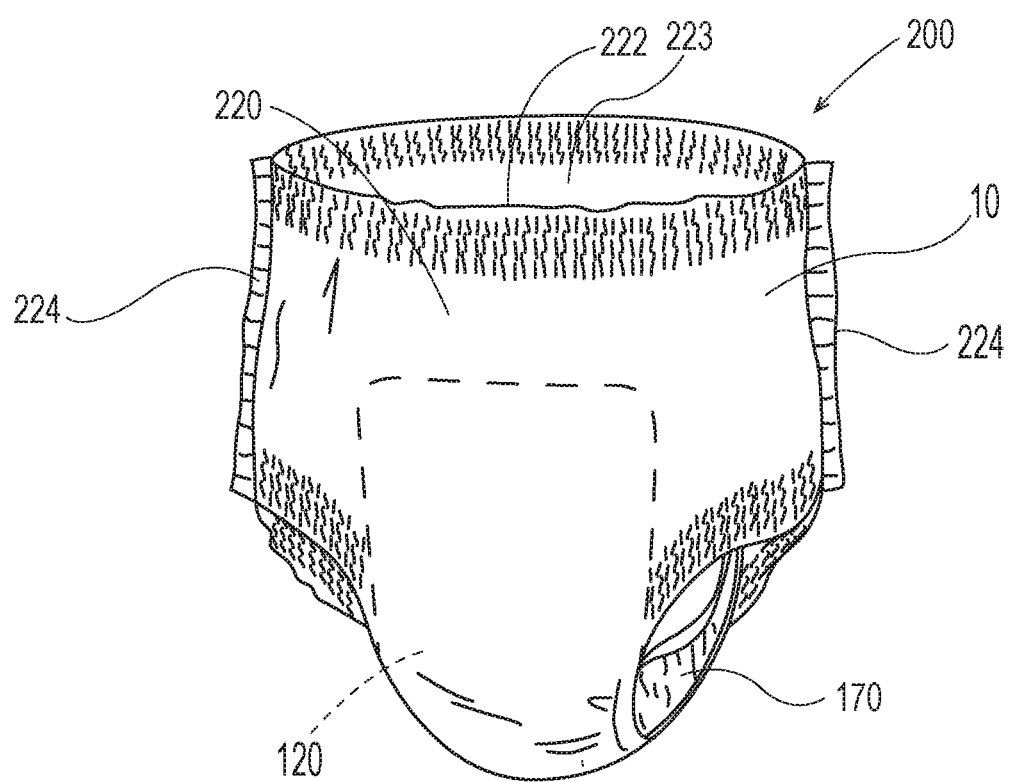
FIG. 7A is a schematic perspective view of an absorbent pant in accordance with a nonlimiting embodiment of the present invention.
Figure 7B:
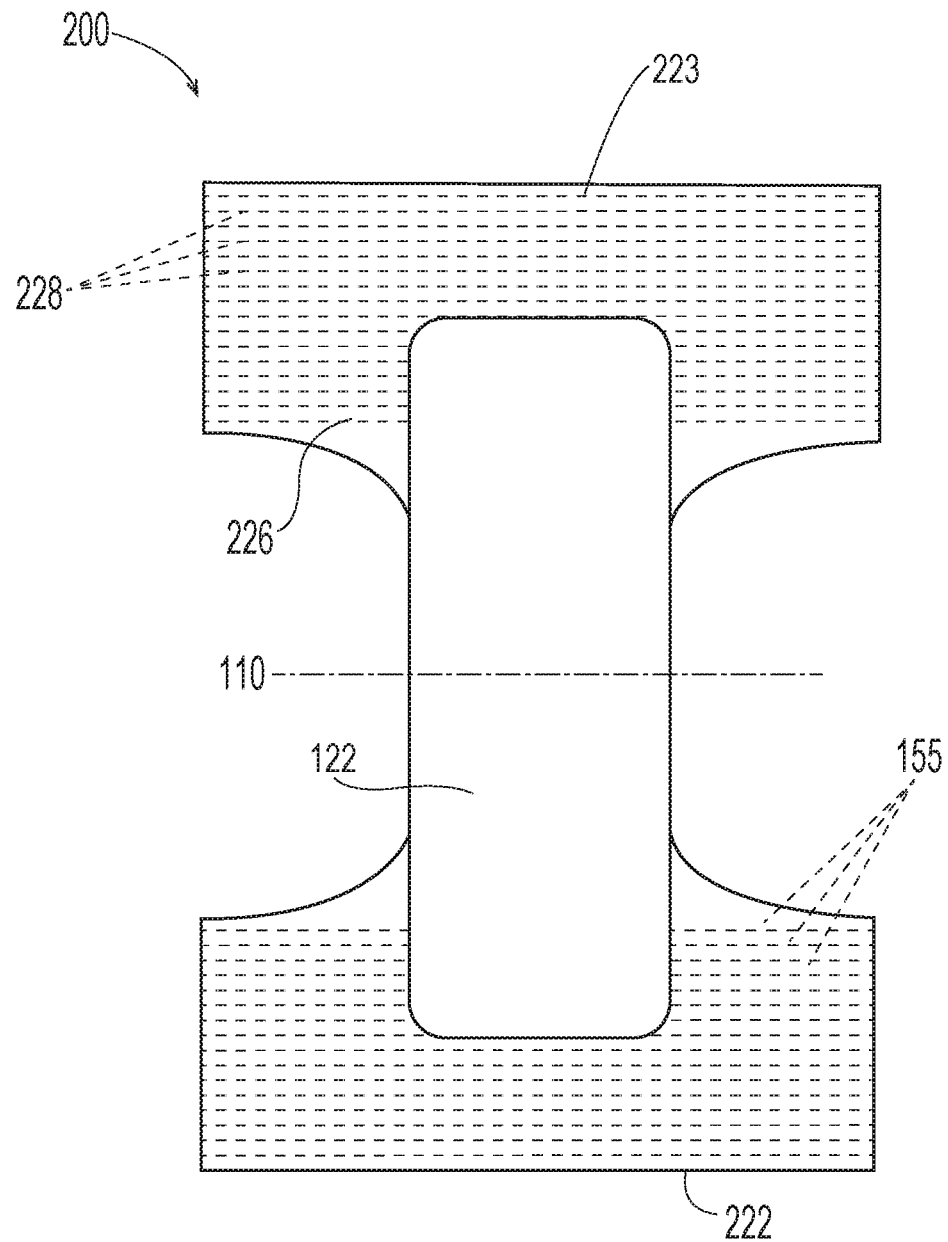
FIG. 7B is an exemplary precursor structure of the pant in FIG. 7A, in an open configuration laid out flat and stretched out laterally against elastic-induced contraction.

In some embodiments, the article 100 may comprise an absorbent pant 200 as shown in FIGS. 7A and 7B. The absorbent pant may comprise include a chassis 120, a belt 220 to be positioned about the wearer's waist, and optionally a leg gasketing system 170. FIG. 7B depicts an exemplary precursor structure of the pant in FIG. 7A, in an open configuration laid out flat and stretched out laterally against elastic-induced contraction. In the final assembly of the pant, the front belt portion 222 is joined to rear belt portion 223 at seams 224, which may be permanent or refastenable. To form the pant 200, the precursor structure may be folded at or about lateral centerline 110 with the topsheet 124 facing inward, and the longitudinal edges of the front 222 and rear 223 belt portions may be joined at seams 224, forming a pant structure having leg openings, front waist edge and rear waist edge. In this way, the pant 200 may comprise a pre-formed, continuous waist opening and pre-formed, continuous leg openings for the wearer at the time of donning the pant 200.

The front and rear belt portions 222, 223 may be the outermost structures forming the front and rear regions of a pant 200. The pant may include an outer wrap 226 wrapping the entirety of the front, crotch and rear regions, and forming an outermost pant-shaped structure. In some embodiments, the outer cover of the backsheet forms the outer wrap. An outer wrap 226 may be formed of one or more sections of nonwoven web and may be cut to a profile providing suitably tailored leg opening edge profiles as desired.

A belt 220 may comprise the laminate 10 of the present invention, having any of the afore-described features including one or more nonwoven layers and one or more elastomeric layers. The laminate layers may be joined by ultrasonic bonding. Belt portions may comprise gathered laminates.

According to some nonlimiting examples, the nonwoven used for a belt portion may include a material that provides good recovery when external pressure is applied and removed.

Elastomeric layers of waist features, such as belt portions, may comprise one or more elastic members 155. The elastic members 155 may be elastomeric fibers, such as LYCRA® fibers available from INVISTA of Wichita, KS, in various decitex levels. The elastic members 155 may also comprise any heat shrinkable elastic material as is well known in the art. Other suitable elastics can be made various other materials including but not limited to: rubbers, styrene ethylbutylene styrene, styrene ethylene propylene styrene, styrene ethylene propylene styrene, styrene butadiene styrene, styrene isoprene styrene, polyolefin elastomers, elastomeric polyurethanes, and other elastomeric materials known in the art, and combinations thereof. In some nonlimiting examples, the elastic members may be extruded strand elastics with any number of strands (or filaments). In some embodiments, the elastic members can have a decitex ranging from 50 to 2000, or any integer value for any decitex value in this range. However, the skilled person may select the appropriate decitex based on the desired contraction and other principles discussed herein. In further embodiments, the elastic members may be in a form of film. Examples of films have been described in prior patent applications (see, for example, U.S. Pat. App. Pub. No. 2010/0040826). The film may be created with a variety of resins combined in at least one of several sublayers, the latter providing different benefits to the film.

In addition, elastic members 155 may take a multitude of configurations. For example, the width may be varied; a single strand or several parallel or non-parallel strands of elastic material may be used; or a variety of shapes may be used including rectilinear and curvilinear; or a variety of cross-sectional shapes can be used (circular, rectangular, square, etc.).

Layers of a waist feature (e.g., belt portion) and/or chassis 120 may be joined together about elastic strands 155 by adhesive deposited between the layers, by thermal bonds, by compression bonds, or by a combination thereof. In other examples, the one or more elastic members may be strips or a section of film formed of elastomeric material. Where the elastic member is elongate, it may be desirable that the longer dimension be laterally oriented, or even substantially aligned with the lateral direction, as strands 155 are depicted in FIG. 7B for example.

A belt portion or other form of waist feature may comprise at least 3 waist elastic members, at least 5 elastic members, at least 10 waist elastic members, or at least 15 waist elastic members, or from about 2 to about 35 waist elastic members, or from about 5 to about 25 waist elastic members, reciting for each range every 1 increment therein.

In one embodiment, adjacent elastic members 155 are spaced a longitudinal distance of at least 3.5 mm apart from one edge of the member to the other edge of the member, optionally at least 4 mm apart; optionally at least 4.5 mm apart; optionally at least 5 mm apart; optionally at least 5.5 mm apart; optionally at least 6 mm apart; optionally at least 6.5 mm apart; optionally at least 7 mm apart; optionally at least 7.5 mm apart; optionally at least 8 mm apart; optionally at least 8.5 mm apart; optionally at least 9 mm apart; optionally at least 9.5 mm apart; optionally at least 10 mm apart; optionally at least 10.5 mm apart; optionally at least 11 mm apart; optionally at least 11.5 mm apart; optionally at least 12 mm apart. The spacing between elastic members may be the same or different across the longitudinal length of the waist feature. For example, the spacing between adjacent elastic members could uniformly be 7 mm or there could be variable spacing (i.e., two adjacent elastic members are separated by 3 mm, another two are separated by 6.5 mm, etc.).

During manufacture of the waist feature, the elastic members 155 may be pre-strained by a desired amount as they are being incorporated into the waist feature. Upon subsequent relaxation of the waist feature, the elastic members will contract laterally toward their unstrained lengths. This may cause layers of the waist feature to gather and form ruffles or rugosities having ridges and valleys generally transverse to the lengths of the elastic members 155 and extending in the z-direction.

In certain embodiments, corners of the front and/or rear belt portion may be trimmed off as suggested in FIG. 7B. The corners may be trimmed off along straight lines, or may be trimmed off along trim paths that are curved and either concave or convex with respect to the remaining area of the belt portion, as may be desired to impart a particular curved leg edge profile. In conjunction with such trimming and the configuration of elastic strands described above, it may be desired to impart bonding between layers along edges of the respective belt portion 222, 223. Such bonding may serve to prevent any separation of the layers along edges that may contribute to creating a ragged appearance, and may also help the rear belt portion more effectively draw inward laterally toward the central chassis 120, under the contractive force of the elastic strands below seams 224. Bonding may be affected by mechanical/compression bonds as described in, for example, U.S. Pat. Nos. 4,854,984 and 4,919,738, by thermal bonds or welds, or by deposits of adhesive between layers. In nonlimiting examples, such bonding may form a pattern along edges. Such bonding may be supplemental to any bonding between layers generally holding the respective belt portion 222, 223 together as a laminate structure.

Side seams 224 may be permanent or refastenable. Permanent seams may be formed between the front belt portion and the rear belt portion by any bonding mechanism wherein the front and rear belt portions may not be forcibly separated without substantial damage to one or both of the front and rear belt portions, or without any included mechanism by which substantial reattachment or refastening may be affected. Bonding forming permanent seams may include compression bonding, thermal bonding/welds, ultrasonic bonding or adhesive bonding. Refastenable seams may be formed between the front belt portion and the rear belt portion by any mechanism configured to permit substantially non-destructive forcible separation of the front and rear belt portions, and subsequent substantial reattachment or refastening at the same locations. One example of such mechanism is a hook-and-loop fastening system, for example, a VELCRO fastening system. A suitably sized and shaped hooks component may be bonded to one of the front or rear belt portions along the longitudinal edges thereof, and a suitably sized and shaped loops component may be bonded to the other of the front or rear belt portions along the longitudinal edges thereof, in positions in which they may be brought together and engaged to form seams 224.

Test Methods

Bond Dimension Test Method

Figure 8:
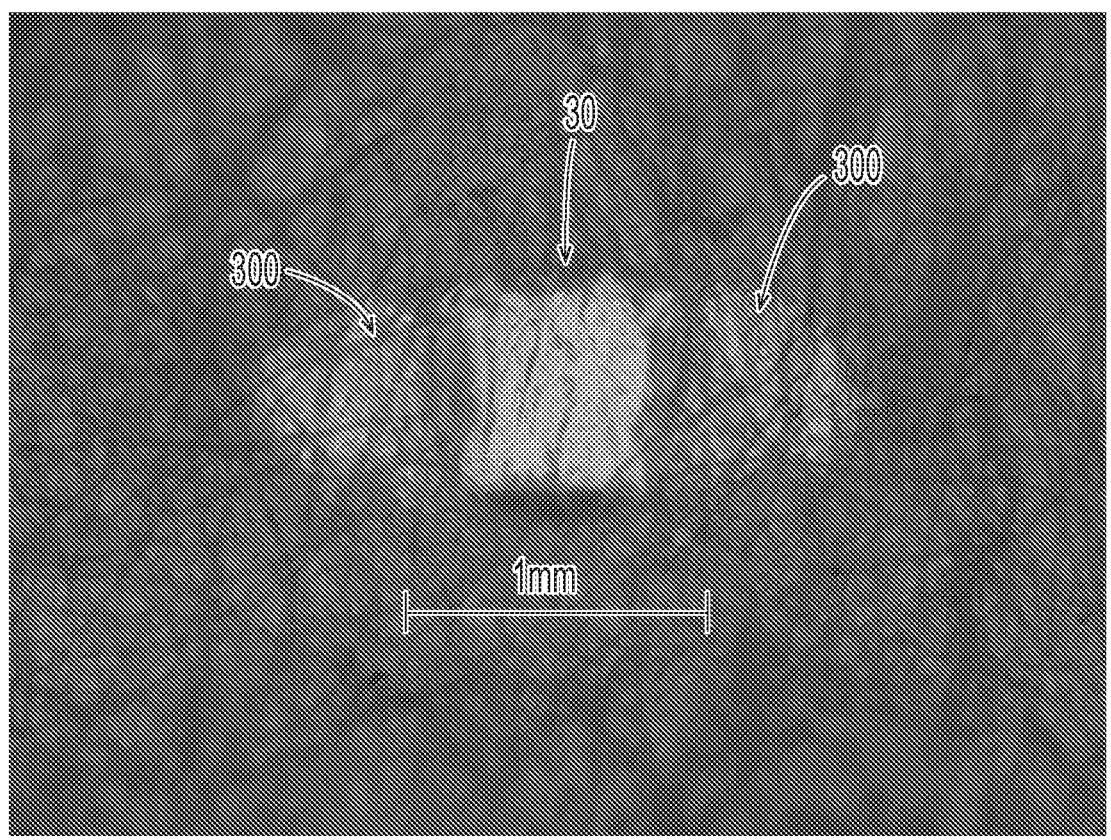
FIG. 8 is a microphotograph of an exemplary bond pattern for illustration of test method procedures.

The Bond Dimension Test is used to measure bond density of the laminate in the various bonding regions. The Bond Dimension Test is performed on transmission light microscopy images generated using a stereolight microscope (such as Zeiss V20 Stereoscope) and attached camera (such as the Carl ZeissAxio Cam MRc5). Measurements are performed using line tool or irregular area tool in Image Pro Plus software (Version 7.0.0.591, Media Cybernetics, USA) calibrated against a scale that was placed within the image when it was acquired. The accuracy of the scale generated by the microscope is checked against a ruler/caliper before images and measurements are acquired. For purposes of this method, a bond is the intentional joining of two or more layers and is the deformed area caused during the bonding process (e.g., the reduced caliper at the site of bonding). It is recognized that in some cases, the deformed area may include one or more apertures. Tears or slits in the elastomeric layer where the nonwovens are not joined are not considered bonds, as shown in FIG. 8 where the bond 30 is the generally square area substantially matching the shape of the nub. On the sides of the bond in FIG. 8 are lighter areas which are film tears 300, where the nonwovens are not bonded within said tears. Such tear areas 300 are not bonds or portions of a bond.

To measure bond dimensions in the elasticized region, the laminate is fully stretched until the wrinkles or corrugations are flattened. Care should be taken to avoid overstretching of the corrugated elastic region, which results in plastic deformation of the nonwovens or plastic substrate.

Specimen Collection

Figure 9:
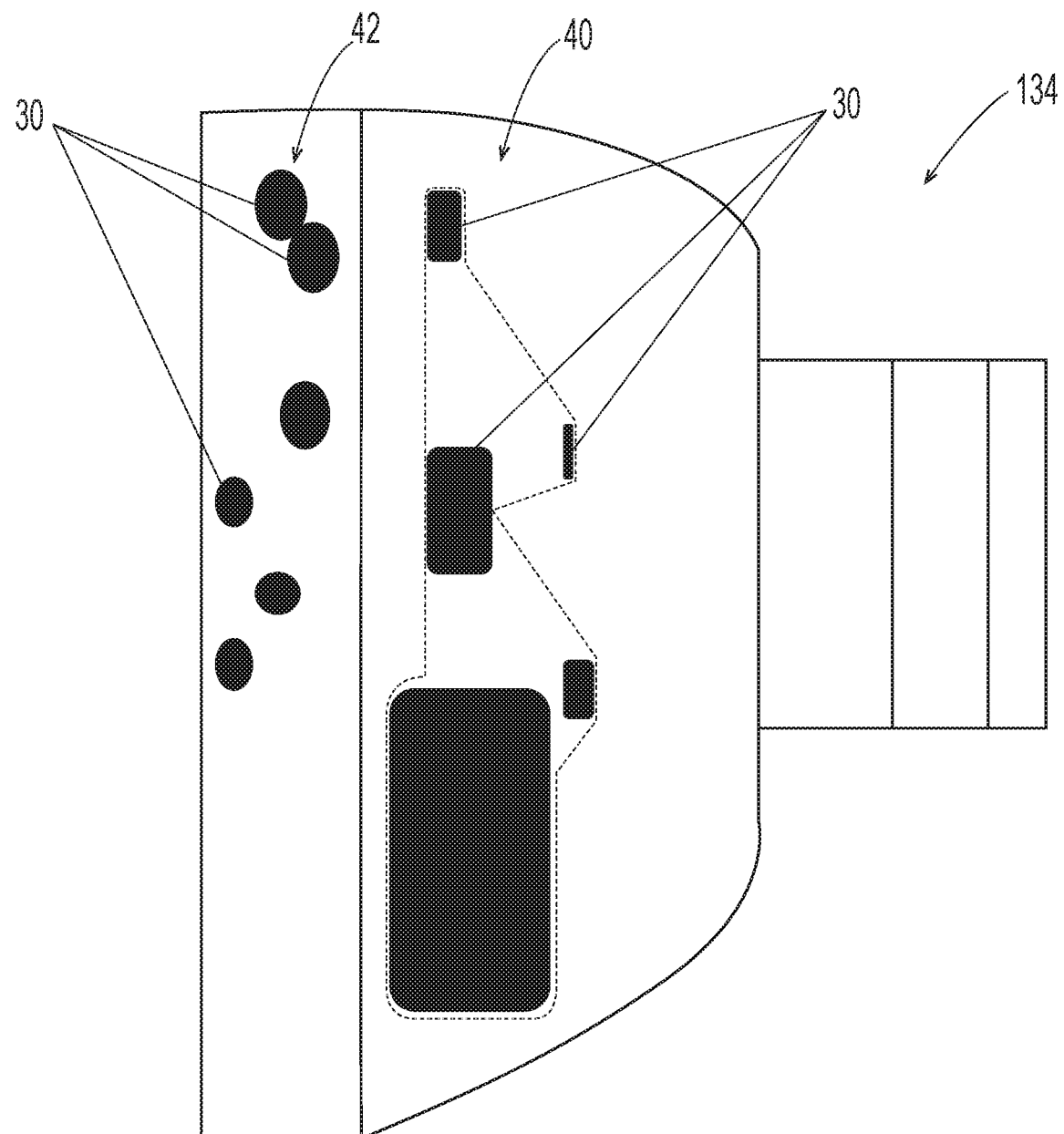
FIG. 9 is a schematic plan view of an ear laminate in accordance with a nonlimiting embodiment, for illustration of test method procedures.

1. Uniform pattern regions: To measure bond density of the bonding region having a uniform pattern, a square specimen of at least 1 cm² area is cut from the patterned bonded region of the laminate. Care should be taken to avoid or measuring collecting specimen from an adjacent region, if it is different. If specimen collection size of 1 cm² square is larger than the patterned region, the specimen is collected in the rectangle shape having a 1 cm² area: the shorter dimension of the patterned region forms one side of the rectangle and the other is selected such a way that rectangle area is 1 cm².
2. Other regions: To measure bond density of a bonding region without a uniform pattern, identify the plurality of bonds of interest and outline the resulting periphery as in FIG. 9. The specimen is collected by cutting along the periphery.
3. To the extent bonding regions are not identifiable in an ear, the ear may be segmented into three longitudinally extending regions: The first region has a width corresponding to the maximum width between the proximate edge of the ear and edge of the chassis bond closest to the distal edge of the ear. The second region has a width corresponding to the maximum width between the distal edge and the edge of the fastener attachment bond closest to the proximate edge of the ear. The third region has a width that extends between the first and second regions. Each region extends longitudinally for the length of the ear in their respective regions and the lengths may vary in the same manner as the ear's length varies in their respective regions.

Figure 10A:
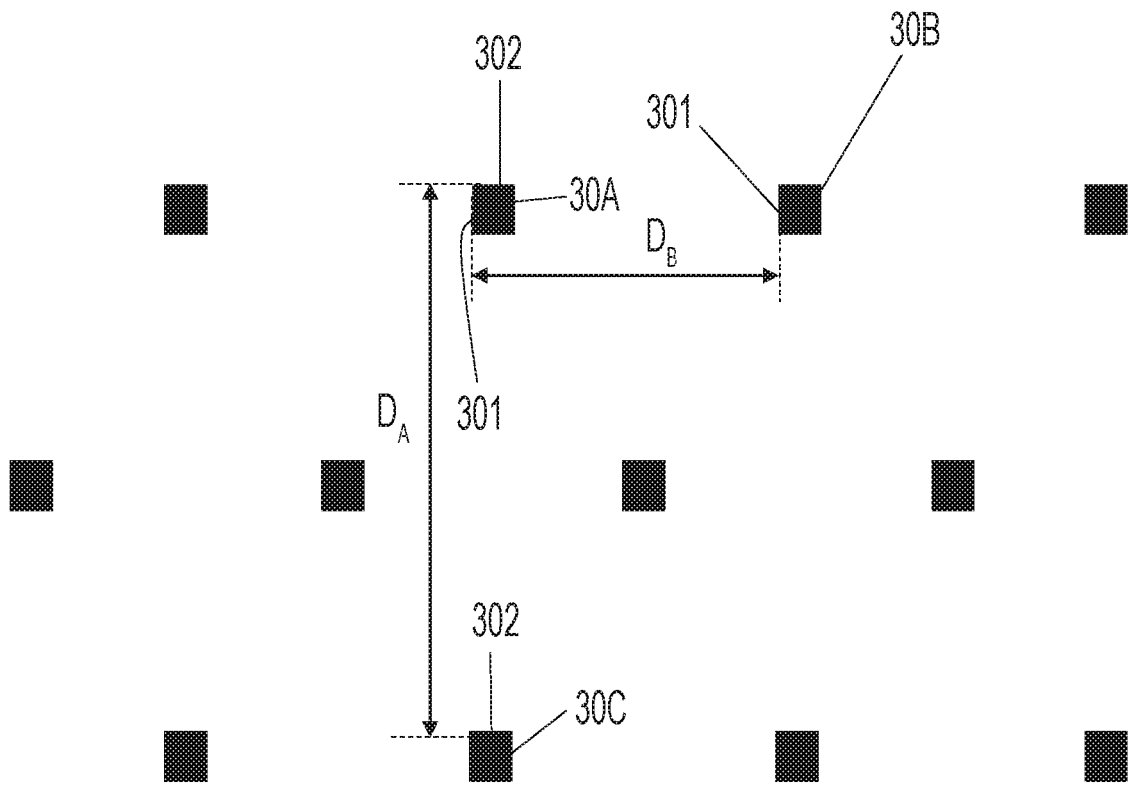

Bond dimensions and separation distances are measured to accuracy of 0.01 mm using a microscope and/or imaging software. A total of five measurements are used and an average Separation Distance (i.e., Maximum Lateral Separation Distance or Maximum Longitudinal Separation Distance) is calculated. The Maximum Lateral Separation Distance is measured between the furthest points on a first longitudinal bond edge 301 of a first bond 30A to a first longitudinal bond edge 301 (i.e., the equivalent edge) of the most laterally proximate second bond 30B, along a line parallel to the lateral axis as shown in FIGS. 10A-10B. The Maximum Longitudinal Separation Distance is measured between the furthest points on a first lateral bond edge 302 of a first bond 30A to a first lateral edge 302 (i.e., the equivalent edge) of the most longitudinally proximate second bond 30C, along a line parallel to the longitudinal axis. To the extent that the rows do not align with the lateral direction of the article, the specimen is to be reoriented such that the rows are aligned with the lateral direction of the article prior to measuring the lateral separation distance. To the extent that the columns do not align with the longitudinal direction of the article, the specimen is to be reoriented such that the columns are aligned with the longitudinal direction of the article prior to measuring the longitudinal separation distance.

For regions without a regular pattern having rows, the Lateral Separation Distances are measured between the furthest points on the adjacent bonds along a line that is 180°±10° of the lateral direction. The largest Lateral Separation Distance in the specimen is taken as the Maximum Lateral Separation Distance. For regions without a regular pattern having columns, the Longitudinal Separation Distances are measured between the furthest points on the adjacent bonds along a line that is 180°±10° of the longitudinal direction. The largest Longitudinal Separation Distance in the specimen is taken as the Maximum Longitudinal Separation Distance.

The Discrete Bond Area is measured using the irregular area tool 15 in Image Pro Plus software or equivalent program by selecting only the lighter area and excluding adjacent periphery that appears as a darker grey scale (as illustrated in FIG. 8). The Average Discrete Bond Area for at least five bonds is calculated. The Aggregate Bond Area is the Average Discrete Bond Area, multiplied by the number of bonds in the 1 cm² specimen area. Bond Density is the Aggregate Bond Area divided by the specimen area (i.e., 1 cm²). The resulting Bond Density is normalized to 1 cm² specimen area and reported.

Tensile Test Method

A suitable tensile tester interfaced with a computer such as MTS model Alliance RT/1 with TestWorks 4® software or equivalent is used. The tensile tester is located in a temperature-controlled room at 22° C.±2° C. and 50±10% relative humidity. The instrument is calibrated according to the manufacturer's instructions. The data acquisition rate is set to at least 50 Hertz. The grips used for the test are wider than the sample. Grips having 50.8 mm width may be used. The grips are air actuated grips designed to concentrate the entire gripping force along a single line perpendicular to the direction of testing stress having one flat surface and an opposing face from which protrudes a half round (radius=6 mm, e.g. part number: 56-163-827 from MTS Systems Corp.) or equivalent grips, to minimize slippage of the sample. The load cell is selected so that the forces measured are between 10% and 90% of the capacity of the load cell used. The initial distance between the lines of gripping force (gauge length) is set at 25.4 mm. The load reading on the instrument is zeroed to account for the mass of the fixture and grips.

A specimen measuring 50.8 mm (along the CD of the web or in the intended stretch direction of the laminate) by 25.4 mm (along the MD of the web or perpendicular to the intended stretch direction of the laminate) is cut either from the article component having the laminate, the component web (with the laminate therein) or the laminate web. The specimen is cut in a way that elasticized region is in the center and is at least 25.4 mm long in CD or in the intended stretch direction of the laminate. In the case when 50.8 mm long sample is not available, a specimen as small as 32 mm in CD or in the intended stretch direction can be used. The specimen is mounted into the grips in a manner such that there is no slack and the load measured is between 0.00 N and 0.02 N. The specimen is mounted in the center of the grips, such that the specimen direction of stretching is parallel to the applied tensile stress. The specimen is gripped in a way that elasticized region covers the entire gage length, i.e. elasticized region starts at the top grip and runs all the way to the bottom grip.

The specimen is extended at 508 mm/min, with a data acquisition rate of at least 50 Hertz, until the specimen breaks, typically >100% strain. The % strain is calculated from the length between grip lines L, and initial gauge length, $L_0$, using the following formula:

$$\% \text{ Strain} = \frac{(L - L_0)}{L_0} \times 100$$

Each specimen is pulled until it ruptures (i.e. the post peak force response reaches a value less than 10% of the peak force). Break is defined as the point where the material fractures or ruptures, and force drops rapidly to zero value.

The testing is repeated for five separate specimens and the average and standard deviation of at least four specimens are reported. If, standard deviation recorded is higher than 5%, a new set of five specimens is run. The averaged values for each of the following are recorded: Elongation at 0.5N Load, the Elongation at 1.5N Load, the Elongation at 3.0N Load, the Load at Peak, and the Elongation at Peak. Elongation data are reported in % strain. Peak Force is normalized by the width of the sample and Load at Peak is reported as N/cm.

Hysteresis Test Method

The instrument is set up as described in the Tensile Test Setup section above. Gage Length and Crosshead Speed are adjusted as per the test and table below. Data acquisition rate is set to at least 50 Hertz.

TABLE 5

|  | Gage Length | Cross Head Speed |
|---|---|---|
| Elastic Definition test | 7 mm | 70 mm/min |
| Sample Hysteresis test | 25.4 mm | 254 mm/min |

Sample Preparation:

For Elastic Definition Test: The specimen is cut with a dimension of 10 mm in the intended stretch direction of the laminate×25.4 mm in the direction perpendicular to the intended stretch direction of the laminate. A specimen is collected from either an inelastic region or from an elastic region.

For Sample Hysteresis Test: The specimen is cut with a dimension of 50.8 mm (or minimum 32 mm) in the intended stretch direction of the laminate×25.4 mm in the direction perpendicular to the intended stretch direction. A specimen is collected from an elastic region in such a way that it has corrugated area of at least 25.4 mm long in the stretch direction.

Test Protocol

1. Pre-Load: Place the specimen in the grips such that the uniform width lies along a direction perpendicular to the gauge length direction. Secure the specimen in the upper grip, let the specimen hang slack, then close the lower grip. For sample hysteresis test, the corrugated length must cover the entire gage length (i.e., between the top grip and the bottom grip, there should not be an inelastic region or dead zone). Set the slack preload at 5 gram/force This means that the data collection starts when the slack is removed (at a constant crosshead speed of 13 mm/min) with a force of 5 gram force. Strain is calculated based on the adjusted gauge length ($l_{ini}$), which is the length of the specimen in between the grips of the tensile tester at a force of 5 gram-force. This adjusted gauge length is taken as the initial specimen length, and it corresponds to a strain of 0%. Percent strain at any point in the test is defined as the change in length relative to the adjusted gauge length, divided by the adjusted gauge length, multiplied by 100.

2. First cycle loading: Pull the specimen to the 100% strain at a constant cross head speed as described in table 5. Record the load at the 75% strain, and at the 100% strain ($F_{ini}$). Record the Length of specimen between the grips on first cycle at the 100% strain ($l_{max}$) to the nearest 0.001 mm.

3. First Hold: Hold the specimen at the 100% strain for 30 seconds. Record the load at the 100% strain ($F_{en}$d) at the end of 30 seconds hold.

4. First cycle unloading: Return the crosshead to its starting position (initial sample length, $l_{ini}$) at a constant cross head speed as described in table 5. Report the unload at the 50% strain.

5. Second Hold: Hold the specimen in the unstrained state for 1 minute.

6. Second cycle loading: Pull the specimen to the 100% strain at a constant cross head speed as described in table 5. Record the Length of specimen between the grips at a second cycle load force of 7 gram-force ($l_{ext}$) to the nearest 0.001 mm 7. Second cycle hold and unload: Next, hold the specimen at the 100% strain for 30 seconds and then return the crosshead to its fresh starting position (before gage length adjustment) at a constant cross head speed as described in table 5.

The testing is repeated for five separate specimens and the average and standard deviation of at least four specimens are reported. If, standard deviation recorded is higher than 5%, a new set of five specimens is run.

The measured and recorded forces, in Newtons (N), are the load forces at 75% and 100% strain in step (2), load force at 100% at the end of step (3), and the unload force at 50% strain in step (4). Recorded average lengths are $l_{ini}$, $l_{max}$, and $l_{ext}$.

Force Relaxation %, which is defined as $(F_{ini}-F_{end})/F_{ini}*100$, is recorded to the nearest 0.01%.

% Set, which is defined as $(l_{ext}-l_{ini}/(l_{max}-l_{ini})*100\%$, is recorded to the nearest 0.01%.

Hysteresis Ratio=Load Force at 75%/Unload Force at 50%

The averaged values for each of the above is reported.

Peel Force Test Method

The instrument is set up as described in the Tensile Test Setup section above. The initial distance between the lines of gripping force (gauge length) is set at 50.8 mm. The load reading on the instrument is zeroed to account for the mass of the fixture and grips.

Sample Preparation:

The specimen is cut either from article component having the laminate, the article component web or the laminate web with a dimension of 25.4 mm in the intended stretch direction of the laminate×152.4 mm in the direction perpendicular to the intended stretch direction of the laminate. A specimen is collected from an elasticized region of the sample, unless specified other ways. For measuring Peel Force in the corrugated area of the elasticized region, the sample is collected from the corrugated area. Similarly, a dead zone sample is collected from the dead zone of the elasticized region. If the specimen is not wide enough or long enough, then follow the procedure as described at the end of this method for cutting and testing samples.

A minimum of five specimens are collected and cut from the same portion of identical absorbent article products or laminate web, and care should be taken to prevent damage of the specimen during the separation process.

Figure 11:
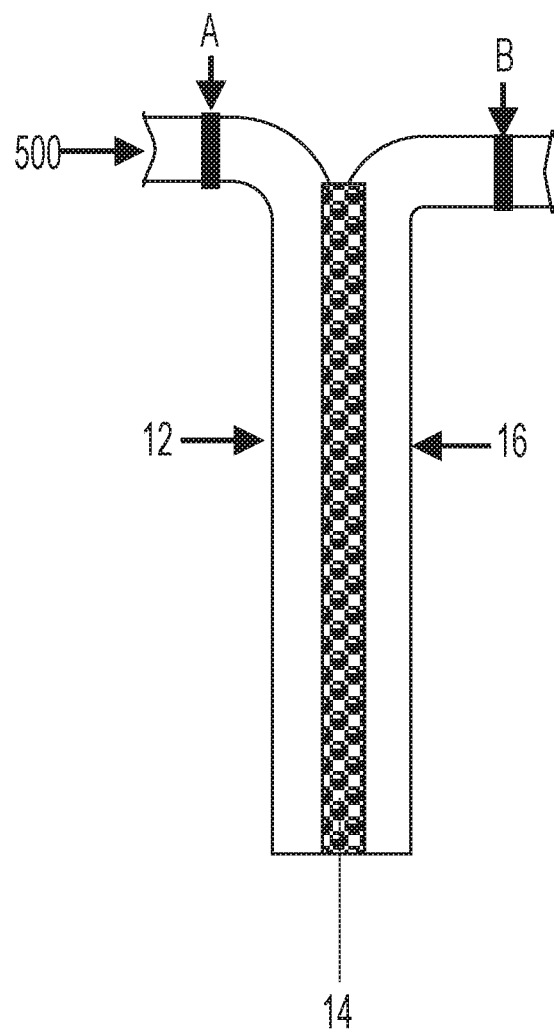
FIG. 11 is a schematic, side elevation view of a specimen for use in the Peel Test Method herein.

Referring to FIG. 11, starting at one of the transverse ends 500 of the specimen, the specimen peel is initiated by delicately separating the first substrate 12 from the second substrate 16 at the bonded junction by using tweezers or delicate fingers, until approximately 30 mm of the first substrate 12 has been separated from second substrate 16 and the elastomeric layer 14.

The specimen is mounted into the grips in a manner such that there is no slack and the load measured is between 0.00 N and 0.02 N. The specimen is mounted in the center of the grips, such that the specimen peeling direction is parallel to the applied tensile stress. The specimen is placed between the grips such that the longitudinal dimension of the bonding region will be perpendicular to the grip apexes, where the first grip is holding the first substrate (Nonwoven) at Grip Line A and the second grip is holding the elastic film and second substrate (Nonwoven) at Grip Line B, thereby peeling the first substrate from the elastic film and the second substrate in a 180° peeling direction. The peel test is initiated, and the specimen is extended at 300 mm/min, with a data acquisition rate of at least 50 Hertz, until the specimens separate completely. The peel displacement of each specimen is reported on the x axis in millimeters of crosshead travel, while the separation force of each specimen is reported on the y axis in Force (gf, grams Force). The separation force (gf) is averaged from 25.4 mm to approximately 127 mm of peel displacement (travel). The Averaged Force is normalized by the specimen bond area width, using the following formula:

$$\text{Peel Force} = \frac{gf}{cm} = \left( \frac{\text{Averaged Force, grams Force}}{\text{Specimen Bond Area Width, cm}} \right)$$

This is reported as the Specimen Peel Force. The arithmetic average of the Specimen Peel Force in gf/cm and standard deviation of at least 4 specimens is recorded and reported as the Average Peel Force (gf/cm). If, standard deviation recorded is higher than 15%, a new set of four specimens is tested.

A skilled artisan should recognize that bonded specimens of other dimensions may be used in the Peel Method. This may require use of different gage length, and separation force is averaged over different peel distance rather than 25.4 mm to 127 mm. The crosshead speed should be kept the same as per the method at 300 mm/min. For example, a sample that is 15 mm wide in stretch direction and 40 mm long in the direction perpendicular to stretch direction can be evaluated using 10 mm gage length. Separation force for such sample should be averaged over peel distance of 10 mm to 50 mm. Separation force should be averaged over minimum 40 mm of peel distance (travel) and should not include first 10 mm of peel data. If the bond area width in the specimen is narrower than specimen width, then the effective bonded area should remain centered in the specimen during the peel test. The averaged separation force should be normalized by the specimen bond area width using the following formula:

$$\text{Peel Force} = \frac{gf}{cm} = \left( \frac{\text{Averaged Force, } gf}{\text{Specimen Bond Area Width, cm}} \right)$$

Air Permeability Test

The air permeability of a laminate or substrate (e.g., film, nonwoven, or article component) is determined by measuring the flow rate of standard conditioned air through a test specimen driven by a specified pressure drop. This test is particularly suited to materials having relatively high permeability to gases, such as nonwovens, apertured laminates and the like. ASTM D737 is used, modified as follows.

A TexTest FX 3300 instrument or equivalent is used, available from Textest AG, Switzerland, or from Advanced Testing Instruments ATI in Spartanburg SC, USA. The procedures described in the Operating Instructions for the TEXTEST FX 3300 Air Permeability Tester manual for the Air Tightness Test and the Function and Calibration Check are followed. If a different instrument is used, similar provisions for air tightness and calibration are made according to the manufacturer's instructions.

The specimen is tested while in a fully stretched state (i.e., no wrinkles or corrugations and no plastic deformation in the plastic substrate(s)).

The test pressure drop is set to 125 Pascal and the 38.3 $cm^2$ area test head (model FX 3300-5) or equivalent is used. The result is recorded to three significant digits. The average of 5 specimens is calculated and reported as the Air Permeability Value ($m^3/m^2$/min).

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article comprising:
    a first waist region, a second waist region and a crotch region disposed between the first and second waist regions;
    a topsheet, a backsheet and an absorbent core disposed between the topsheet and the backsheet; and
    a laminate comprising an elasticized region and being disposed in an ear or a waist feature disposed in one of the first or second waist regions;
    wherein the laminate further comprises:
        a first nonwoven and a second nonwoven and an elastomeric material sandwiched between said first and second nonwovens in the elasticized region;
        a bonding region comprising a plurality of discrete bonds and a bond density of at least 4%, wherein the bonding region at least partially overlaps the elastomeric material; and
    wherein the bonding region at least partially overlaps a dead zone.

2. The absorbent article of claim 1 wherein the discrete bonds are disposed in a grid pattern.

3. The absorbent article of claim 1 wherein in the bonding region, adjacent bonds are separated by a Maximum Lateral Separation Distance of 3 mm or less and a Maximum Longitudinal Separation Distance of 4 mm of less.

4. The absorbent article of claim 1 wherein the plurality of discrete bonds comprises a plurality of ultrasonic bonds.

5. The absorbent article of claim 1 wherein one or more of the discrete bonds comprises a Discrete Bond Area of 0.3 mm$^2$ or greater.

6. The absorbent article of claim 1 wherein the discrete bonds are disposed in a staggered pattern.

7. The absorbent article of claim 6 wherein adjacent bonds are separated by a Maximum Longitudinal Separation Distance of 2 mm or less.

8. The absorbent article of claim 1 wherein the laminate comprises a Hysteresis Ratio of at least 2.

9. An absorbent article comprising:
    a first waist region, a second waist region and a crotch region disposed between the first and second waist regions;
    a topsheet, a backsheet and an absorbent core disposed between the topsheet and the backsheet; and
    an ear disposed in one of the first or second waist regions, the ear comprising:
        a laminate comprising:
            a first nonwoven and a second nonwoven and an elastomeric material sandwiched between said first and second nonwovens in an elasticized region;
            a first bonding region comprising a bond density of at least 4.25%; and
            a second bonding region comprising a second bond density that is less than the first bond density.

10. The absorbent article of claim 9, wherein in the elasticized region, the laminate comprises a 50% Unload Force of at least 0.9 N according to the Hysteresis Test Method herein.

11. The absorbent article of claim 10, wherein the 50% Unload Force is at least 0.95 N.

12. The absorbent article of claim 9, wherein the second bonding region at least partially overlaps a corrugated area.

13. The absorbent article of claim 9 further comprising a dead zone, wherein the first bonding region at least partially overlaps the dead zone and wherein the dead zone comprises a second Average Peel Force that is at least 90 gf/cm.

14. The absorbent article of claim 9 wherein the second bond density is at least 60% less than the first bond density.

15. An absorbent article comprising:
    a first waist region, a second waist region and a crotch region disposed between the first and second waist regions;
    a topsheet, a backsheet and an absorbent core disposed between the topsheet and the backsheet; and
    an elasticized laminate having layers joined by a plurality of ultrasonic bonds, wherein the elasticized laminate comprise:
        a first nonwoven and an elastomeric material; and
        a first bonding region comprising a first bond density of at least 4% and an Elongation at 1.5 N Load of 20% or greater, wherein the first bonding region at least partially overlaps a dead zone.

16. The absorbent article of claim 15 wherein the Elongation at 1.5 N Load is 25% or greater.

17. The absorbent article of claim 15 further comprising a second bonding region, wherein the second bonding region comprises a second bond density, and wherein the second bond density is 60% or less of the first bond density.

18. The absorbent article of claim 17 wherein the second bonding region at least partially overlaps a corrugated area.

19. The absorbent article of claim 15 wherein the bonding region comprises a Load at Peak of 8 N/cm or greater.

20. The absorbent article of claim 15 wherein the bonding region comprises an Elongation at Peak of at least 330%.

* * * * *